United States Patent
Sotoyama et al.

(10) Patent No.: US 6,805,977 B2
(45) Date of Patent: Oct. 19, 2004

(54) CONDENSED EIGHT-RING AROMATIC COMPOUND, AND ORGANIC EL ELEMENT AND ORGANIC EL DISPLAY USING THE SAME

(75) Inventors: Wataru Sotoyama, Kawasaki (JP); Hiroyuki Sato, Kawasaki (JP); Azuma Matsuura, Kawasaki (JP); Toshiaki Narusawa, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 10/104,013

(22) Filed: Mar. 25, 2002

(65) Prior Publication Data

US 2003/0082404 A1 May 1, 2003

(30) Foreign Application Priority Data

Aug. 29, 2001 (JP) ........................................ 2001-259684
Nov. 27, 2001 (JP) ........................................ 2001-361504

(51) Int. Cl.[7] ........................ H05B 33/12; C09K 11/06; C07C 211/00
(52) U.S. Cl. ........................ 428/690; 428/917; 313/504; 313/506; 252/301.16; 564/426
(58) Field of Search ........................ 428/690, 917; 313/506, 504; 252/301.16; 564/426

(56) References Cited

U.S. PATENT DOCUMENTS 6,203,933 B1 * 3/2001 Nakaya et al. ............... 428/690
6,329,083 B1 * 12/2001 Toguchi et al. .............. 428/690

FOREIGN PATENT DOCUMENTS

| EP | 0 868 110 A1 | 9/1998 |
| JP | A 5-32596 | 2/1993 |
| JP | 5-190283 | 7/1993 |
| JP | A 5-194943 | 8/1993 |
| JP | A 6-219973 | 8/1994 |
| JP | A 07-110940 | 4/1995 |
| JP | A 8-259940 | 10/1996 |
| JP | A 10-289786 | 10/1998 |
| JP | 11-87057 | 3/1999 |
| JP | 11-273864 | 10/1999 |
| JP | 2000-26337 | 1/2000 |
| JP | 2001-102172 | 4/2001 |
| JP | A 2001-118682 | 4/2001 |

OTHER PUBLICATIONS

Patent Abstracts of Japan of JP 05–222361 dated Aug. 31, 1993.
Patent Abstracts of Japan of JP 06–136359 dated May 17, 1994.
Patent Abstracts of Japan of JP 06–140156 dated May 20, 1994.
Patent Abstracts of Japan of JP 06–219973 dated Aug. 9, 1994.
Patent Abstracts of Japan of JP 07–101911 dated Apr. 18, 1995.
Patent Abstracts of Japan of JP 07–282975 dated Oct. 27, 1995.
Patent Abstracts of Japan of JP 09–188874 dated Jul. 22, 1997.

(List continued on next page.)

*Primary Examiner*—Marie Yamnitzky
*Assistant Examiner*—C S Thompson
(74) *Attorney, Agent, or Firm*—Staas & Halsey LLP

(57) ABSTRACT

The object of the present invention is to provide an organic EL element which utilizes a novel condensed eight-ring aromatic compound, and has high color purity of red light and excellent light-emitting efficiency, light-emitting luminance and the like. The organic EL element of the present invention has, in between a positive electrode and a negative electrode, an organic thin-film layer including a light-emitting layer. The organic thin-film layer contains the condensed eight-ring aromatic compound which has a number of regions where substituents can be introduced is any of 14, 16 and 18, and the condensed eight-ring aromatic compound has a point-symmetrical skeleton.

31 Claims, 3 Drawing Sheets

OTHER PUBLICATIONS

Patent Abstracts of Japan of JP 10–067984 dated Mar. 10, 1998.
Patent Abstracts of Japan of JP 10–088122 dated Apr. 7, 1998.
Patent Abstracts of Japan of JP 10–255985 dated Sep. 25, 1998.
Patent Abstracts of Japan of JP 11–185962 dated Jul. 9, 1999.
Patent Abstracts of Japan of JP 11–199864 dated Jul. 27, 1999.
Patent Abstracts of Japan of JP 11–214152 dated Aug. 6, 1999.
Patent Abstracts of Japan of JP 11–329719 dated Nov. 30, 1999.
Patent Abstracts of Japan of JP 11–354283 dated Dec. 24, 1999.
Patent Abstracts of Japan of JP 2000–136379 dated May 16, 2000.
Patent Abstracts of Japan of JP 2000–164363 dated Jun. 16, 2000.
Patent Abstracts of Japan of JP 2000–212466 dated Aug. 2, 2000.
Patent Abstracts of Japan of JP 2000–231987 dated Aug. 22, 2000.
Patent Abstracts of Japan of JP 2000–243575 dated Sep. 8, 2000.
Patent Abstracts of Japan of JP 2000–273056 dated Oct. 3, 2000.
Patent Abstract of USP 6358633.
Patent Abstracts of Japan of JP 2001–003044 dated Jan. 9, 2001.
Patent Abstracts of Japan of JP 2001–023778 dated Jan. 26, 2001.
Patent Abstracts of Japan of JP 2001–052861 dated Feb. 23, 2001.
Patent Abstracts of Japan of JP 2001–064529 dated Mar. 13, 2001.
Patent Abstracts of Japan of JP 2001–089681 dated Apr. 3, 2001.
Patent Abstracts of Japan of JP 2001–102174 dated Apr. 13, 2001.
Patent Abstracts of Japan of JP 2001–118682 dated Apr. 27, 2001.
Patent Abstracts of Japan of JP 2001–126874 dated May 11, 2001.
Patent Abstracts of Japan of JP 2001–131541 dated May 15, 2001.
Patent Abstracts of Japan of JP 2000–212466 dated Aug. 2, 2000.
Patent Abstracts of Japan of JP 05–222361 dated Aug. 31, 1993.
A. Bloess et al., "Microscopic Structure in a Shpol'skii System: A Single–Molecule Study of Dibenzanthanthrene in n–Tetradecane", p. 703, Chemical Abstracts, vol. 134, No. 23, Jun. 4, 2001, Columbus Ohio.
Becker, Ralph S. et al., "Electron Affinities and Ionization Potentials of Aromatic Hydrocarbons", *Journal of the American Cheical Society*, vol. 85, Aug. 5, 1963, pp. 2210–2214.
C.W. Tang and S.A. VanSlyke, "Organic electroluminescent diodes"; Applied Physics Letters; vol. 51 (12); pp. 913–915 (1987).
C.W. Tang, S. A. VanSlyke, and C. H. Chen; "Electroluminescence of doped organic thin films"; Journal of Applied Physics; vol. 65(9); pp. 3610–3616 (1989).

* cited by examiner

Schematic View of Passive Matrix Panel

Circuit Diagram of
Active Matrix Panel

CONDENSED EIGHT-RING AROMATIC COMPOUND, AND ORGANIC EL ELEMENT AND ORGANIC EL DISPLAY USING THE SAME

CROSS-REFERENCE TO RELATED APPLICATIONS

This application is based upon and claims priority of Japanese Patent Applications No. 2001-259684, filed in Aug. 29, 2001, and Japanese Patent Application No. 2001-361504, filed in Nov. 27, 2001, the contents being incorporated herein by reference.

BACKGROUND OF THE INVENTION

1. Field of the Invention

The present invention relates to a condensed eight-ring aromatic compound which is suitably used in an organic EL element, an organic EL element using the condensed eight-ring aromatic compound, and an organic EL display using the organic EL element.

2. Description of the Related Art

Organic EL elements have features such as self-lighting, high-speed response, and the like, and application thereof to flat panel displays is expected. When a full-color flat panel display is realized by using organic EL elements, organic EL elements which can emit lights of the three primary colors (blue (B), green (G) and red (R)), respectively, are required.

For example, an organic EL element using a DCM dye is disclosed as an organic EL element which can emit red (R) light in C. W. Tang, S. A. VanSlyke, and C. H. Chen, "Journal of Applied Physics", Vol. 65, 3610 (1989). Further, organic EL elements, which use a porphin compound or a porphine compound which can emit red light, have been proposed in Japanese Patent Application Laid-Open (JP-A) No. 9-13024 (Japanese Patent Application No. 7-160676), JP-A No. 9-296166 (Japanese Patent Application No. 8-111437), JP-A No. 11-251061 (Japanese Patent Application No. 10-50464), JP-A No. 11-251062 (Japanese Patent Application No. 10-50465), a Japanese National Re-Publication (International Publication No. WO98/00474, Japanese Patent Application No. 10-503982), and the like. Moreover, an organic EL element using a bisanthrene compound which can emit red light has been disclosed in JP-A No. 11-144868 (Japanese Patent Application No. 9-303047).

However, with these organic EL elements, there is the problem that the color of the emitted light and the light-emitting efficiency are insufficient in actual use, and further improvements in actual use are required.

SUMMARY OF THE INVENTION

The present invention focuses on addressing these concerns, overcoming the aforementioned drawbacks of the prior art, and achieving the following object. Namely, an object of the present invention is to provide a condensed eight-ring aromatic compound which has high color purity of red light and excellent light-emitting efficiency, light-emitting luminance and the like and which is suitable for an organic EL element, an organic EL element which uses the condensed eight-ring aromatic compound and has high color purity of red light and excellent light-emitting efficiency, light-emitting luminance and the like, and an organic EL display which is high-performance and utilizes the organic EL element.

As a result of intensive studies carried out by the present inventors in order to overcome the above drawbacks, the present inventors discovered the following. Namely, specific condensed eight-ring aromatic compounds have high color purity of red light and excellent light-emitting efficiency, light-emitting luminance and the like, and are particularly suited for organic EL elements which are used for emitting red light. An organic EL element and an organic EL display using this condensed eight-ring aromatic compound have high color purity of red light and excellent light-emitting efficiency, light-emitting luminance and the like, and are high-performance, and can emit light at a higher luminance than conventional structures. Further, the condensed eight-ring aromatic compound has excellent transportability of positive holes (carrier) or electrons. An organic EL element and an organic EL display which use the condensed eight-ring aromatic compound in at least one of a positive hole transporting layer and an electron transporting layer have high color purity of red light and excellent light-emitting efficiency, light-emitting luminance and the like, are high-performance, and can emit light at a higher luminance than conventional structures.

In the condensed eight-ring aromatic compound of the present invention, a number of regions where substituents can be introduced is any of 14, 16 and 18, and the condensed eight-ring aromatic compound has a point-symmetrical skeleton. (However, excluding such cases in which the regions where substituents can be introduced are all hydrogen atoms.)

An organic EL element of the present invention comprises an organic thin-film layer including a light-emitting layer in between a positive electrode and a negative electrode, and the organic thin-film layer contains a condensed eight-ring aromatic compound, wherein the condensed eight-ring aromatic compound comprises a structure which has a number of regions where substituents can be introduced in any of 14, 16 and 18, and has a point-symmetrical skeleton.

The organic EL display of the present invention uses the organic EL element of the present invention.

DESCRIPTION OF THE PREFERRED EMBODIMENTS

<Condensed Eight-Ring Aromatic Compound>

Figure 1:
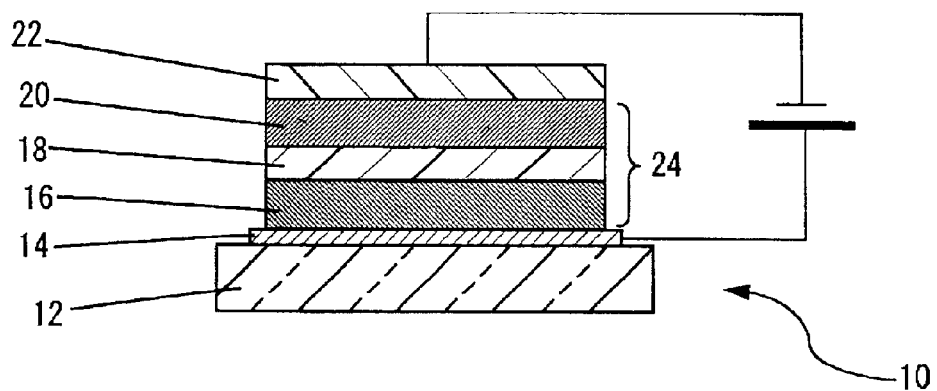
FIG. 1 is a schematic explanatory view for explaining an example of a layer structure in an organic EL element of the present invention.

In the condensed eight-ring aromatic compound comprising a structure which has a number of regions where substituents can be introduced in any of 14, 16 and 18, and has a point-symmetrical skeleton (However excluding such cases in which the regions where substituents can be introduced are all hydrogen atoms).

Examples of the condensed eight-ring aromatic compound are condensed eight-ring aromatic hydrocarbon compounds and derivatives thereof. Specifically, compounds expressed by any of following structural formulas (1) through (3) can be suitably used. Note that the condensed eight-ring aromatic compound expressed by structural formula (1) is a dinaphtho(2':3'-3:4)(2":3"-8:9)pyrene compound (hereinafter simply called "dinaphthopyrene compound"), the condensed eight-ring aromatic compound expressed by structural formula (2) is a 2,3,8,9-dibenzanthanthrene compound (hereinafter simply called "dibenzanthanthrene compound"), and the condensed eight-ring aromatic compound expressed by structural formula (3) is a peri-naphthacenonaphthacene compound (hereinafter simply called "naphthacenonaphthacene compound").

Structural Formula (1)

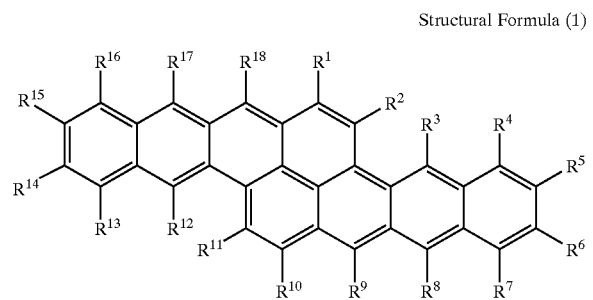

In structural formula (1), $R^1$ through $R^{18}$ may be the same or may be different to each other, and represent hydrogen atoms or substituents (but cases in which all are hydrogen atoms are excluded).

Structural Formula (2)

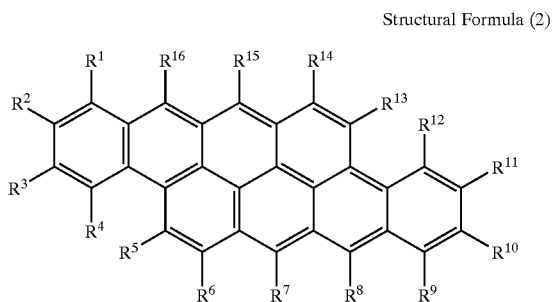

In structural formula (2), $R^1$ through $R^{16}$ may be the same or may be different to each other, and represent hydrogen atoms or substituents (but cases in which all are hydrogen atoms are excluded).

Structural Formula (3)

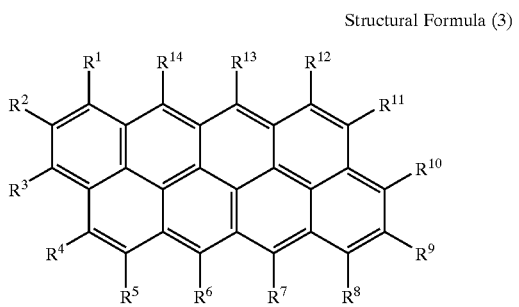

In structural formula (3), $R^1$ through $R^{14}$ may be the same or may be different to each other, and represent hydrogen atoms or substituents (but cases in which all are hydrogen atoms are excluded).

The substituents are not particularly limited provided that the color emission of the condensed eight-ring aromatic compound exhibits red (R) (i.e., provided that the light-emitting wavelength is about 580 to 780 nm), and may be appropriately selected in accordance with the object. It is preferable to select, for example, a halogen atom, a hydroxyl group, a cyano group, an alkyl group, an alkoxyl group, an aryl group, an aryloxy group, an arylamino group, a diarylamino group, or the like.

When the condensed eight-ring aromatic compound has these substituents, the operation and effects of the substituents are as follows.

If the substituents are halogen atoms or alkyl groups, these substituents increase the affinity of the condensed eight-ring aromatic compound and a host compound which will be described later.

If the substituents are hydroxyl groups, cyano groups, alkoxyl groups or aryloxy groups, these substituents shift the color of the emitted light of the condensed eight-ring aromatic compound in the direction of longer wavelengths.

If the substituents are aryl groups, the substituents suppress the concentration quenching due to the association between the molecules, by making the flat mother core of the condensed eight-ring aromatic compound be a stereo structure.

If the substituents are arylamino groups or diarylamino groups, these substituents shift the color of the emitted light of the condensed eight-ring aromatic compound in the direction of longer wavelengths, and improve the positive hole transportability of the condensed eight-ring aromatic compound, and suppress the concentration quenching due to the association between the molecules, by making the flat mother core of the condensed eight-ring aromatic compound be a stereo structure.

Examples of the halogen atom are fluorine, chlorine, bromine, and the like.

The alkyl group is not particularly limited, and can be appropriately selected in accordance with the object. Suitable examples are straight chain, branched or cyclic alkyl groups having from 1 to 10 carbon atoms. Specific suitable examples include methyl, ethyl, propyl, isopropyl, butyl, isobutyl, tertiary butyl, pentyl, isopentyl, hexyl, isohexyl, heptyl, isoheptyl, octyl, isooctyl, nonyl, isononyl, decyl, isodecyl, cyclopentyl, cyclobutyl, cyclopropyl, cyclohexyl, cycloheptyl, cyclooctyl, cyclononyl, cyclodecyl, and the like.

The alkoxy group is expressed by —OR (where R represents the aforementioned alkyl groups). Examples include methoxy, ethoxy, propoxy, isopropoxy, cyclopropoxy, butoxy, isobutoxy, cyclobutoxy, cyclopentoxy, cyclohexyloxy, and the like.

The aryl group is not particularly limited, and can be appropriately selected in accordance with the object. Suitable examples include monocyclic aromatic ring groups, groups formed by four or fewer aromatic rings being bonded together, groups having five or fewer condensed aromatic rings and whose total number of carbon, oxygen, nitrogen, and sulfur atoms is 30 or less, and the like.

The monocyclic aromatic ring group is not particularly limited, and can be appropriately selected in accordance with the object. Examples include phenyl, tolyl, xylyl, cuminyl, styryl, mesityl, cinnamyl, phenethyl, benzhydryl, and the like. These may be substituted by substituents.

The groups formed by four or fewer aromatic rings being bonded together are not particularly limited, and can be appropriately selected in accordance with the object. Examples include naphthyl, anthryl, phenanthryl, indenyl, azulenyl, benzanthracenyl, and the like. These may be substituted by substituents.

The groups having five or fewer condensed aromatic rings and whose total number of carbon, oxygen, nitrogen, and sulfur atoms is 30 or less are not particularly limited, and can be appropriately selected in accordance with the object. Examples include pyrrolyl, furyl, thienyl, pyridyl, quinolyl, isoquinolyl, imadazoyl, pyridinyl, pyrrolopyridinyl, thiazoyl, pyrimidinyl, thiophenyl, indolyl, quinolinyl, pyrinyl, adenyl, and the like, and may be substituted by substituents.

The aryl groups in the above aryloxy group, arylamino group, and diarylamino group are the same as the aforementioned aryl groups.

Suitable examples of the arylamino group are those expressed by the following formula for example.

In the formula, $Ar^1$ represents an aryl group. Examples of the aryl group are the aforementioned aryl groups. $R^{19}$ represents a hydrogen atom, or a straight chain, branched or cyclic alkyl group having from 1 to 10 carbon atoms. Examples of such alkyl groups are those listed above.

Suitable examples of the diarylamino group are those expressed by the following formula for example.

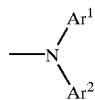

In the formula, $Ar^1$ and $Ar^2$ may be the same or different, and each represents an aryl group. Suitable examples of the aryl group are the above-listed aryl groups.

The condensed eight-ring aromatic compound can suitably used in an organic EL element, and can be suitably used in an organic thin-film layer, particularly a light-emitting layer or the like, of the organic EL element.

It is preferable that at least one of $R^1$ through $R^{18}$ in above structural formula (1), at least one of $R^1$ through $R^{16}$ in above structural formula (2), or at least one of $R^1$ through $R^{14}$ in above structural formula (3) is selected from aryl groups, arylamino groups and diarylamino groups. In this case, the condensed eight-ring aromatic compound has the advantages that it has high color purity of red light and excellent light-emitting efficiency, light-emitting luminance and the like, and it can suitably be used in an organic EL element.

When at least one of $R^1$ through $R^{18}$ in above structural formula (1), at least one of $R^1$ through $R^{16}$ in above structural formula (2), or at least one of $R^1$ through $R^{14}$ in above structural formula (3) is an aryl group, the condensed eight-ring aromatic compound is an aryl condensed eight-ring aromatic compound having excellent electron transportability, and can suitably be used in at least one of an electron transporting layer and a light-emitting layer in the organic EL element.

When at least one of $R^1$ through $R^{18}$ in above structural formula (1), at least one of $R^1$ through $R^{16}$ in above structural formula (2), or at least one of $R^1$ through $R^{14}$ in above structural formula (3) is an arylamino group, the condensed eight-ring aromatic compound is an arylamino condensed eight-ring aromatic compound having excellent positive hole (carrier) transportability. Moreover, when at least one of $R^1$ through $R^{18}$ in above structural formula (1), at least one of $R^1$ through $R^{16}$ in above structural formula (2), or at least one of $R^1$ through $R^{14}$ in above structural formula (3) is a diarylamino group, the condensed eight-ring aromatic compound is a diarylamino condensed eight-ring aromatic compound having excellent positive hole (carrier) transportability. Each can be suitably used in at least one of a positive hole transporting layer and a light-emitting layer in the organic EL element.

When, in structural formula (1), $R^1$ through $R^8$ and $R^{10}$ through $R^{17}$ are hydrogen atoms and $R^9$ and $R^{18}$ are selected from phenyl groups, phenylamino groups, and diphenylamino groups (i.e., in the case of "structure 1"), the compound is stable. Therefore, the condensed eight-ring aromatic compound (the dinaphthopyrene compound) can be suitably used in the organic EL element. $R^9$ and $R^{18}$ being the same is preferable from the standpoint that the effects are marked.

Similarly to above, in structural formula (1), a case in which $R^2$ through $R^9$ and $R^{11}$ through $R^{18}$ are hydrogen atoms and $R^1$ and $R^{10}$ are selected from phenyl groups, phenylamino groups, and diphenylamino groups (i.e., the case of "structure 2"), a case in which $R^1$ through $R^7$, $R^9$ through $R^{16}$, and $R^{18}$ are hydrogen atoms and $R^8$ and $R^{17}$ are selected from phenyl groups, phenylamino groups, and diphenylamino groups (i.e., the case of "structure 3"), a case in which $R^1$ through $R^6$, $R^8$ through $R^{15}$, and $R^{17}$ through $R^{18}$ are hydrogen atoms and $R^7$ and $R^{16}$ are selected from phenyl groups, phenylamino groups, and diphenylamino groups (i.e., the case of "structure 4"), and the like are also preferable.

When, in structural formula (2), $R^1$ through $R^6$, $R^8$ through $R^{14}$, and $R^{16}$ are hydrogen atoms and $R^7$ and $R^{15}$ are selected from phenyl groups, phenylamino groups, and diphenylamino groups (i.e., in the case of "structure 1"), the compound is stable. Therefore, the condensed eight-ring aromatic compound (the dibenzanthanthrene compound) can be suitably used in the organic EL element. $R^7$ and $R^{15}$ being the same is preferable from the standpoint that the effects are marked.

Similarly to above, in structural formula (2), a case in which $R^1$ through $R^5$, $R^7$ through $R^{13}$, and $R^{15}$ through $R^{16}$ are hydrogen atoms and $R^6$ and $R^{14}$ are selected from phenyl groups, phenylamino groups, and diphenylamino groups (i.e., the case of "structure 2"), a case in which $R^1$ through $R^7$ and $R^9$ through $R^{15}$ are hydrogen atoms and $R^8$ and $R^{16}$ are selected from phenyl groups, phenylamino groups, and diphenylamino groups (i.e., the case of "structure 3"), a case in which $R^2$ through $R^8$ and $R^{10}$ through $R^{16}$ are hydrogen atoms and $R^1$ and $R^9$ are selected from phenyl groups, phenylamino groups, and diphenylamino groups (i.e., the case of "structure 4"), and the like are also preferable.

When, in structural formula (3), $R^1$ through $R^5$, $R^7$ through $R^{12}$, and $R^{14}$ are hydrogen atoms and $R^6$ and $R^{13}$ are selected from phenyl groups, phenylamino groups, and diphenylamino groups (i.e., in the case of "structure 1"), the compound is stable. Therefore, the condensed eight-ring aromatic compound (naphthacenonaphthacene) can be suitably used in the organic EL element. $R^6$ and $R^{13}$ being the same is preferable from the standpoint that the effects are marked.

Similarly to above, in structural formula (3), a case in which $R^1$ through $R^4$, $R^6$ through $R^{11}$, and $R^{13}$ through $R^{14}$ are hydrogen atoms and $R^5$ and $R^{12}$ are selected from phenyl groups, phenylamino groups, and diphenylamino groups (i.e., the case of "structure 2"), a case in which $R^1$ through $R^6$ and $R^8$ through $R^{13}$ are hydrogen atoms and $R^7$ and $R^{14}$ are selected from phenyl groups, phenylamino groups, and diphenylamino groups (i.e., the case of "structure 3"), a case in which $R^2$ through $R^7$ and $R^9$ through R14 are hydrogen atoms and $R^1$ and $R^8$ are selected from phenyl groups, phenylamino groups, and diphenylamino groups (i.e., the case of "structure 4"), and the like are also preferable.

In structural formulas (1) through (3), if the types and the numbers of the substituents are the same, the difference in the absorption peak wavelengths due to differences in the positions of the substituents is generally small. For example, when the absorption peak positions are estimated by molecular orbital computation using a molecular orbital computation program (WinMOPAC V3.0) manufactured by Fujitsu Ltd., in the case of a diphenylnaphthopyrene compound in which two substituents are phenyl groups in structures 1 through 4 in the structural formula (1), the absorption peak wavelength of the diphenylnaphthopyrene compound of the structure 1 is 508 nm, the absorption peak wavelength of the diphenylnaphthopyrene compound of the structure 2 is 503 nm, the absorption peak wavelength of the diphenylnaphthopyrene compound of the structure 3 is 498 nm, and the absorption peak wavelength of the diphenylnaphthopyrene compound of the structure 4 is 492 nm. Further, in the case of a diphenyldibenzanthanthrene compound in which two substituents are phenyl groups in structures 1 through 4 in structural formula (2), the absorption peak wavelength of the diphenyldibenzanthanthrene compound of the structure 1 is 534 nm, the absorption peak wavelength of the diphenyldibenzanthanthrene compound of the structure 2 is 522 nm, the absorption peak wavelength of the diphenyldibenzanthanthrene compound of the structure 3 is 533 nm, and the absorption peak wavelength of the diphenyldibenzanthanthrene compound of the structure 4 is 521 nm.

The condensed eight-ring aromatic compound of the present invention can suitably be used in various fields, and is particularly suitably used in the organic EL element and the organic EL display of the present invention which will be described hereinafter.

<Organic EL Element>

An organic EL element of the present invention comprises an organic thin-film layer including a light-emitting layer in between a positive electrode and a negative electrode, and the organic thin-film layer contains a condensed eight-ring aromatic compound, wherein the condensed eight-ring aromatic compound comprises a structure which has a number of regions where substituents can be introduced in any of 14, 16 and 18, and has a point-symmetrical skeleton.

Suitable examples of the condensed eight-ring aromatic compound are those expressed by any of following structural formulas (1) through (3). The condensed eight-ring aromatic compound expressed by the structural formula (1) is a dinaphthopyrene compound. The condensed eight-ring aromatic compound expressed by the structural formula (2) is a dibenzanthanthrene compound. The condensed eight-ring aromatic compound expressed by the structural formula (3) is a naphthacenonaphthacene compound.

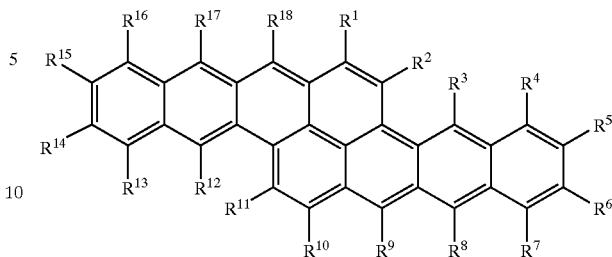

Structural Formula (1)

In structural formula (1), $R^1$ through $R^{18}$ may be the same or may be different to each other, and represent hydrogen atoms or substituents. Examples of the substituents are those listed above.

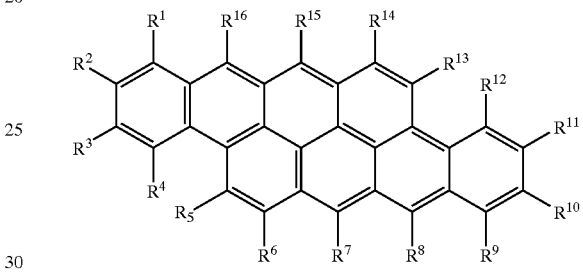

Structural Formula (2)

In structural formula (2), $R^1$ through $R^{16}$ may be the same or may be different to each other, and represent hydrogen atoms or substituents. Examples of the substituents are those listed above.

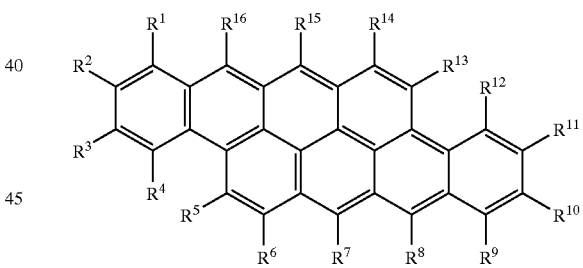

Structural Formula (3)

In structural formula (3), $R^1$ through $R^{14}$ may be the same or may be different to each other, and represent hydrogen atoms or substituents. Examples of the substituents are those listed above.

The condensed eight-ring aromatic compound is contained in the organic thin-film layer, is preferably contained in at least one of the electron transporting layer, the positive hole transporting layer, and the light-emitting layer in the organic thin-film layer, is more preferably contained in the light-emitting layer, and is particularly preferably contained in the electron transporting layer or in the light-emitting layer and the electron transporting layer, or in the positive hole transporting layer or in the light-emitting layer and the positive hole transporting layer.

When the condensed eight-ring aromatic compound is contained in the light-emitting layer and the electron transporting layer or in the light-emitting layer and the positive hole transporting layer, the light-emitting layer and the electron transporting layer, or the light-emitting layer and the positive hole transporting layer, may be separate layers, or may be provided as a single layer which is a light-emitting and electron transporting layer, or which is a light-emitting and positive hole transporting layer.

As the condensed eight-ring aromatic compound which is contained the light-emitting layer, in structural formula (1), it is preferable that at least one of $R^1$ through $R^{18}$ is selected from aryl groups, arylamino groups and diarylamino groups. It is more preferable that $R^1$ through $R^8$ and $R^{10}$ through $R^{17}$ are hydrogen atoms and $R^9$ and $R^{18}$ are selected from phenyl groups, phenylamino groups and diphenylamino groups. It is particularly preferable that $R^9$ and $R^{18}$ are the same.

In structural formula (2), it is preferable that at least one of $R^1$ through $R^{16}$ is selected from aryl groups, arylamino groups and diarylamino groups. It is more preferable that $R^1$ through $R^6$, $R^8$ through $R^{14}$ and $R^{16}$ are hydrogen atoms and $R^7$ and $R^{15}$ are selected from phenyl groups, phenylamino groups and diphenylamino groups.

It is particularly preferable that $R^7$ and $R^{15}$ are the same.

In structural formula (3), it is preferable that at least one of $R^1$ through $R^{14}$ is selected from aryl groups, arylamino groups and diarylamino groups. It is more preferable that $R^1$ through $R^5$, $R^7$ through $R^{12}$ and $R^{14}$ are hydrogen atoms and $R^6$ and $R^{13}$ are selected from phenyl groups, phenylamino groups and diphenylamino groups. It is particularly preferable that $R^6$ and $R^{13}$ are the same.

In these cases, in the above-described preferable cases, the organic EL element is advantageous with regard to the point that it has high color purity of red light and excellent light-emitting efficiency, light-emitting luminance and the like. In the above-described more preferable cases and particularly preferable cases, the condensed eight-ring aromatic compound is stable, and therefore, the organic EL element is advantageous with respect to the fact that it has excellent durability.

As the arylamino group, those expressed by the above formula are preferable. As the diarylamino group, those expressed by the above formula are preferable.

In the condensed eight-ring aromatic compound contained in the electron transporting layer, or contained in the electron transporting layer and the light-emitting layer, in the structural formula (1), it is preferable that at least one of $R^1$ through $R^{18}$ is an aryl group. It is more preferable that $R^1$ through $R^8$ and $R^{10}$ through $R^{17}$ are hydrogen atoms and $R^9$ and $R^{18}$ are phenyl groups. It is particularly preferable that $R^9$ and $R^{18}$ are the same.

In the structural formula (2), it is preferable that at least one of $R^1$ through $R^{16}$ is an aryl group. It is more preferable that $R^1$ through $R^6$, $R^8$ through $R^{14}$ and $R^{16}$ are hydrogen atoms and $R^7$ and $R^{15}$ are phenyl groups. It is particularly preferable that $R^7$ and $R^{15}$ are the same.

In the structural formula (3), it is preferable that at least one of $R^1$ through $R^{14}$ is an aryl group. It is more preferable that $R^1$ through $R^5$, $R^7$ through $R^{12}$ and $R^{14}$ are hydrogen atoms and $R^6$ and $R^{13}$ are phenyl groups. It is particularly preferable that $R^6$ and $R^{13}$ are the same.

In these cases, in the above-described preferable cases, the condensed eight-ring aromatic compound is an aryl condensed eight-ring aromatic compound having excellent electron transportability. The organic EL element is advantageous with respect to the point that it has high color purity of red light and excellent light-emitting efficiency, light-emitting luminance and the like. In the above-described more preferable cases and particularly preferable cases, the condensed eight-ring aromatic compound is stable, and therefore, the organic EL element is advantageous with respect to the fact that it has excellent durability.

In the condensed eight-ring aromatic compound contained in the positive hole transporting layer, or contained in the positive hole transporting layer and the light-emitting layer, in the structural formula (1), it is preferable that at least one of $R^1$ through $R^{18}$ is either an arylamino group and a diarylamino group. It is more preferable that $R^1$ through $R^8$ and $R^{10}$ through $R^{17}$ are hydrogen atoms and $R^9$ and $R^{18}$ are either phenylamino groups or diphenylamino groups. It is particularly preferable that $R^9$ and $R^{18}$ are the same.

In the structural formula (2), it is preferable that at least one of $R^1$ through $R^{16}$ is selected from arylamino groups and diarylamino groups. It is more preferable that $R^1$ through $R^6$, $R^8$ through $R^{14}$ and $R^{16}$ are hydrogen atoms and $R^7$ and $R^{15}$ are either phenylamino groups or diphenylamino groups. It is particularly preferable that $R^7$ and $R^{15}$ are the same.

In the structural formula (3), it is preferable that at least one of $R^1$ through $R^{14}$ is selected from arylamino groups and diarylamino groups. It is more preferable that $R^1$ through $R^5$, $R^7$ through $R^{12}$ and $R^{14}$ are hydrogen atoms and $R^6$ and $R^{13}$ are either phenylamino groups or diphenylamino groups. It is particularly preferable that $R^6$ and $R^{13}$ are the same.

In these cases, in the above-described preferable cases, the condensed eight-ring aromatic compound is an arylamino condensed eight-ring aromatic compound or a diarylamino condensed eight-ring aromatic compound having excellent positive hole (carrier) transportability. The organic EL element is advantageous with respect to the point that it has high color purity of red light and excellent light-emitting efficiency, light-emitting luminance and the like. In the above-described more preferable cases and particularly preferable cases, the condensed eight-ring aromatic compound is stable, and therefore, the organic EL element is advantageous with respect to the fact that it has excellent durability.

It is preferable that the light-emitting layer contain, in addition to the condensed eight-ring aromatic compound, a host compound.

The host compound is preferably a compound whose light-emitting wavelength is in the vicinity of the light absorption wavelength of the condensed eight-ring aromatic compound. Among these, because the light absorption wavelength of the condensed eight-ring aromatic compound is 500 to 650 nm, compounds, whose light absorption wavelength is at the shorter wavelength side of the condensed eight-ring aromatic compound and whose light-emitting wavelength is in a vicinity of the light absorption wavelength of the condensed eight-ring aromatic compound, are preferable. Specifically, the aluminum quinoline complex (Alq) (main light-emitting wavelength=530 nm) expressed by the following structural formula, 9,9'-bianthryl (main light-emitting wavelength=460 nm) expressed by the following structural formula, 4,4'-bis(9-carbazolyl)-biphenyl (CBP) (main light-emitting wavelength=380 nm) expressed by the following structural formula, 4,4'-bis(2,2'-diphenylvinyl)-1,1'-biphenyl (DPVBi) (main light-emitting wavelength=470 nm) expressed by the following structural formula, p-sexiphenyl (main light-emitting wavelength=400 nm) expressed by the following structural formula, 1,3,6,8-tetraphenylpyrene (main light-emitting wavelength=440 nm) expressed by the following structural formula, N,N'-dinaphthyl-N,N'-diphenyl-[1,1'-biphenyl]-4,4'-diamine (NPD) (main light-emitting wavelength=430 nm) expressed by the following structural formula, and the like are preferable. The Aluminum quinoline complex (Alq) is particularly preferable.

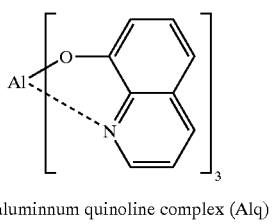

aluminnum quinoline complex (Alq)

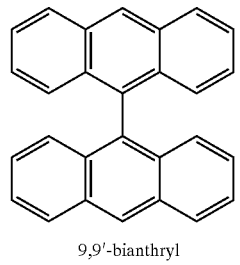

9,9'-bianthryl

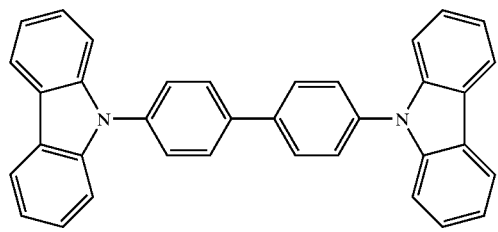

CBP

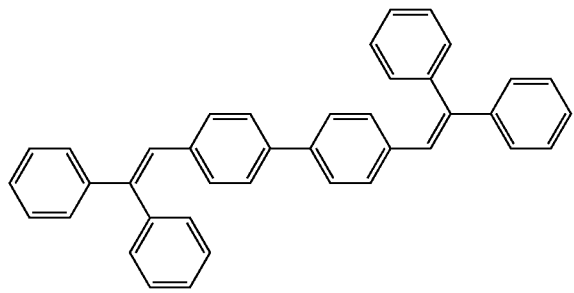

DPVBi

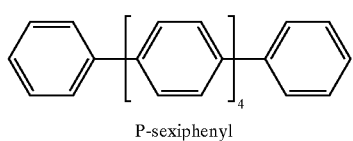

P-sexiphenyl

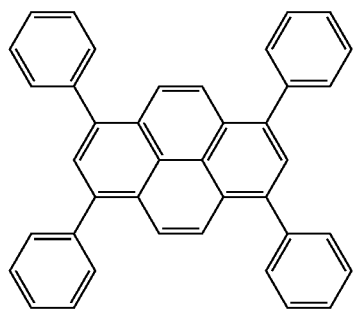

1,3,6,8-tetraphenylpyrene

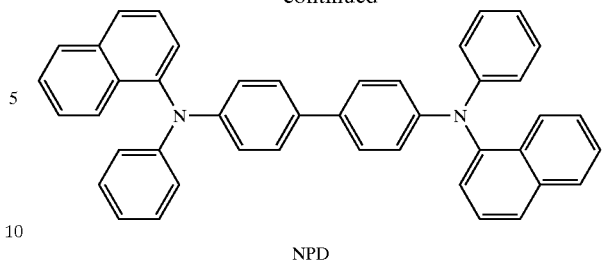

NPD

The host compound, such as the aluminum quinoline complex (Alq) or the like, may have a substituent which is appropriately selected within a range in which the overlapping of the light-emitting wavelength of the host compound on the absorption wavelength of the condensed eight-ring aromatic compound is not eliminated. For example, in the case of the aluminum quinoline complex (Alq), the methyl substituents expressed by the following structural formulas, or the like can suitably be used.

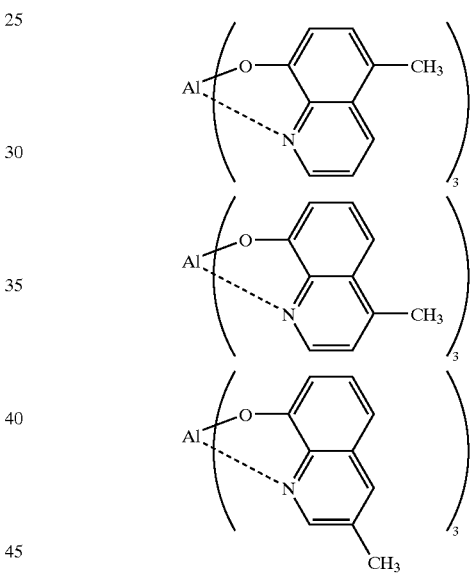

When the light-emitting layer contains the host compound, a material having an excellent film forming ability can be selected as the host compound. Thus, there is the advantage that the light-emitting layer can have an excellent film forming ability regardless of the film forming ability of the condensed eight-ring aromatic compound itself. Further, in the light-emitting layer, when the recombination site, at which the positive holes injected from the positive electrode and the electrons injected from the negative electrode recombine, is the host compound, first, the host compound is excited. Then, in cases in which the light-emitting wavelength of the host compound and the absorption wavelength of the guest compound (the condensed eight-ring aromatic compound) overlap, the excitation energy effectively moves from the host compound to the guest compound (the condensed eight-ring aromatic compound). The host compound returns to the ground state without emitting light, and only the guest compound (the condensed eight-ring aromatic compound) which has moved to an excited state releases the excitation energy as red light. Thus, this is advantageous in that emission of red light of a high color purity is obtained, and the light-emitting efficiency, light-emitting luminance and the like are excellent. Generally when the light emitting molecules exist alone or in high density in the thin layer, generates an interaction between the light emitting molecules referred to as "concentration quenching" which is a light emission efficiency deterioration phenomenon caused by the molecules coming in closer contact with each other. However, in the aforementioned light-emitting layer, the condensed eight-ring aromatic compound is dispersed at a relatively low concentration in the host compound, the aforementioned "concentration quenching" is effectively suppressed, and the light-emitting efficiency is excellent.

The light-emitting layer may contain n types of host compounds (wherein n represents an integer of 1 or more). In this case, given that the n types of host compounds are the first host compound, the second host compound, . . . , the (n−1) th host compound, and the nth host compound in order from the host compound with the shortest light-emitting wavelength, it is preferable that the light-emitting wavelength of the first host compound is in a vicinity of the light absorption wavelength of the second host compound, the light-emitting wavelength of the second host compound is in a vicinity of the light absorption wavelength of the third host compound, . . . , the light-emitting wavelength of the (n−1) th host compound is in a vicinity of the light absorption wavelength of the nth host compound, and the light-emitting wavelength of the nth host compound is in a vicinity of the light absorption wavelength of the condensed eight-ring aromatic compound.

Among the host compounds, a combination of aluminum quinoline complex (Alq) (main light-emitting wavelength= 530 nm) and rubrene (main light absorption wavelength= 530 nm; main light-emitting wavelength=560 nm), and the like are preferable. The light absorption wavelength of the condensed eight-ring aromatic compound is 500 to 650 nm. Thus, a combination of (use of both of) two host compounds which are aluminum quinoline complex (Alq), whose main light-emitting wavelength is 530 nm, and rubrene, whose main light absorption wavelength is 530 nm and whose main light-emitting wavelength is 560 nm and which is expressed by the following structural formula, is more preferable. In this case, since the number of host compound is 2 (i.e., when n=2), the first host compound is aluminum quinoline complex (Alq), and the second host compound is rubrene, the excitation energy effectively moves from the aluminum quinoline complex (Alq) to the rubrene, and from the rubrene to the condensed eight-ring aromatic compound, the aluminum quinoline complex (Alq) and the rubrene hardly emit light, a red light of high color purity could be obtained.

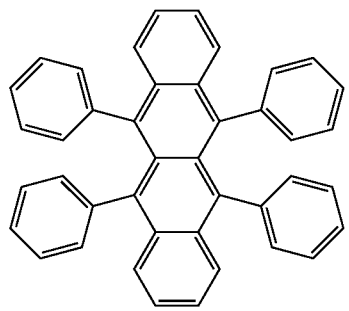

Note that the n types of host compounds such as aluminum quinoline complex (Alq), rubrene, and the like may have substituents which are appropriately selected within the range of not deteriorating the light-emitting efficiency, light-emitting luminance, and the like of the condensed eight-ring aromatic compound. For example, in the case of rubrene, suitable examples of substituents are those represented by the following structural formula, or the like.

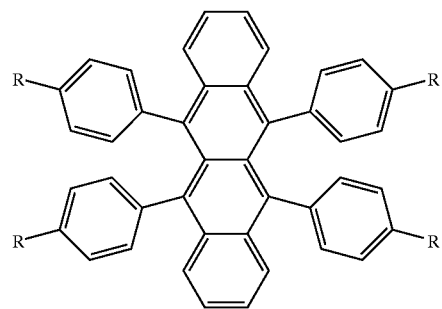

In this structural formula, R represents a substituent. Examples of the substituent are a methyl group, a tertiary butyl group, a phenyl group, and the like.

When the light-emitting layer contains n types of host compounds, materials having an excellent film forming ability can be selected as the first host compound through the nth host compound. Thus, there is the advantage that the light-emitting layer can have an excellent film forming ability regardless of the film forming ability of the condensed eight-ring aromatic compound itself. Further, in the light-emitting layer, when the recombination site, at which the positive holes injected from the positive electrode and the electrons injected from the negative electrode recombine, is the kth host compound, first, the kth host compound is excited. Then, in a case in which the light-emitting wavelength of the kth host compound and the absorption wavelength of the (k+1)th host compound overlap, and the light-emitting wavelength of the (k+1)th host compound and the absorption wavelength of the (k+2) th host compound overlap, . . . , and the light-emitting wavelength of the nth host compound and the absorption wavelength of the guest compound (the condensed eight-ring aromatic compound) overlap, the excitation energy effectively moves from the host compounds to the guest compound (the condensed eight-ring aromatic compound). The host compounds return to the ground state without emitting light, and only the guest compound (the condensed eight-ring aromatic compound) which has moved to an excited state releases the excitation energy as red light. Thus, this is advantageous in that emission of red light of a high color purity is obtained, and the light-emitting efficiency, light-emitting luminance and the like are excellent. Further, at the light-emitting layer, the condensed eight-ring aromatic compound is dispersed at a relatively low concentration in the first host compound through the nth host compound, the aforementioned "concentration quenching" is effectively suppressed, and the light-emitting efficiency is excellent.

The amount of the host compound contained in the light-emitting layer is, with respect to 1 mol of the condensed eight-ring aromatic compound, usually around 4 mol or more, and 10 mol or more is preferable, and 50 mol or more is more preferable.

When the amount of the host compound contained in the light-emitting layer is around 50 mol % or more, improvement in the light-emitting efficiency, light-emitting luminance, and the like of the condensed eight-ring aromatic compound can be seen. In the preferable range, the improvement is sufficient, and in the aforementioned more preferable range, the improvement is marked.

When there are n types of host compounds, among the n types of host compounds and preferably among two types of host compounds, the contained amount in the light-emitting layer of the host compound which has a light-emitting wavelength in a vicinity of the absorption wavelength of the condensed eight-ring aromatic compound is, with respect to 1 mol of the condensed eight-ring aromatic compound, preferably about 0.5 mol or more, and more preferably 1 mol or more, and particularly preferably 3 mol or more.

When the contained amount of the host compound in the light-emitting layer is around 0.5 mol % or more, improvement in the light-emitting efficiency, light-emitting luminance, and the like of the condensed eight-ring aromatic compound can be seen. In the preferable range, the improvement is sufficient, and in the aforementioned more preferable range, the improvement is marked.

The light-emitting layer in the organic EL element of the present invention can, at the time an electrical field is applied, inject positive holes from the positive electrode, a positive hole injecting layer, the positive hole transporting layer or the like, and can inject electrons from the negative electrode, an electron injecting layer, the electron transporting layer or the like, and provides a site for recombination of the positive holes and the electrons. It suffices for the light-emitting layer to have the function of making the condensed eight-ring aromatic compound (light-emitting molecules), which exhibits emission of red light, emit light due to the recombination energy which is generated at the time of recombination. The light-emitting layer may, in addition to the condensed eight-ring aromatic compound, contain another light-emitting material provided that the aforementioned emission of red light does not deteriorate.

Suitable examples of the other light-emitting material are materials which exhibit emission of red light. Examples include the nitrobenzothiazole azo compounds disclosed in JP-A No. 9-272863, the europium complexes disclosed in JP-A No. 9-272864 and JP-A No. 10-158639, and the like.

The other light-emitting material may be contained in the same layer as the condensed eight-ring aromatic compound, or may be contained in a different layer. In the latter case, the light-emitting layer has a multilayer structure.

The light-emitting layer can be formed in accordance with known methods. For example, the light-emitting layer can be suitably formed by a vapor deposition method, a wet-type film forming method, an MBE (molecular beam epitaxy) method, a cluster ion beam method, a molecule accumulating method, an LB method, a printing method, a transfer method, or the like.

Among these, a vapor deposition method is preferable from the standpoints that no organic solvents are used and the problem of waste liquid processing does not arise, and that the vapor deposition method is inexpensive and easy, and efficient manufacturing can be carried out. However, in a case in which the organic thin-film layer is designed to be a single layer structure, for example, in a case in which the organic thin-film layer is formed as a positive hole transporting and light-emitting and electron transporting layer, a wet-type film forming method is preferable.

The vapor deposition method is not particularly limited, and can be appropriately selected from known vapor deposition methods in accordance with the object. Examples include a vacuum vapor deposition method, a low resistance heating vapor deposition method, a chemical vapor deposition method, a physical vapor deposition method, and the like. Examples of the chemical vapor deposition method are a plasma CVD method, a laser CVD method, a heat CVD method, a gas source CVD method, and the like. Formation of the light-emitting layer by a vapor deposition method can suitably be carried out by, for example, vacuum vapor deposition of the condensed eight-ring aromatic compound, and in a case in which the light-emitting layer contains a host compound in addition to the condensed eight-ring aromatic compound, by simultaneously depositing the condensed eight-ring aromatic compound and the host compound by vacuum vapor deposition.

The wet-type film forming method is not particularly limited, and can be appropriately selected from known wet-type film forming methods in accordance with the object. Examples include an ink jet method, a spin coating method, a kneader coating method, a bar coating method, a blade coating method, a casting method, a dipping method, a curtain coating method, and the like.

In the case of the wet-type film forming method, a solution in which the material of the light-emitting layer is dissolved or dispersed together with a resin component can be used (can be applied or the like). Examples of the resin component include polyvinyl carbazole, polycarbonate, polyvinyl chloride, polystyrene, polymethyl methacrylate, polyester, polysulfone, polyphenylene oxide, polybutadiene, hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, and the like.

Formation of the light-emitting layer by a wet-type film forming method may suitably be carried out, for example, by using (applying and drying) a solution (coating liquid) in which the condensed eight-ring aromatic compound and the resin material (which is used as needed) are dissolved in a solvent, or, in a case in which the light-emitting layer contains a host compound in addition to the condensed eight-ring aromatic compound, by using (applying and drying) a solution (coating liquid) in which the condensed eight-ring aromatic compound, the host compound and the resin material (which is used as needed) are dissolved in a solvent.

The thickness of the light-emitting layer is preferably 1 to 50 nm, and more preferably 3 to 20 nm.

When the thickness of the light-emitting layer falls within the above preferable numerical range, the purity of the red light emitted by the organic EL element is high, and the light-emitting efficiency and light-emitting luminance are sufficient. When the thickness of the light-emitting layer falls within the above more preferable numerical range, these features are marked.

The organic EL element of the present invention has, between the positive electrode and the negative electrode, an organic thin-film layer which contains the light-emitting layer. The organic EL element may include other layers, such as a protective layer or the like, in accordance with the object.

The organic thin-film layer has at least the light-emitting layer, and if needed, may also include a positive hole injecting layer, a positive hole transporting layer, an electron transporting layer, or the like.

—Positive Electrode—

The positive electrode is not particularly limited, and can be appropriately selected in accordance with the object. The positive electrode preferably can supply positive holes (carrier) to the organic thin-film layer. Specifically, when the organic thin-film layer has only the light-emitting layer, it is preferable that the positive electrode can supply positive holes to the light-emitting layer. When the organic thin-film layer also has a positive hole transporting layer, it is preferable that the positive electrode can supply positive holes to the positive hole transporting layer. When the organic thin-film layer also has a positive hole injecting layer, it is preferable that the positive electrode can supply positive holes (or carrier) to the positive hole injecting layer.

The material of the positive electrode is not particularly limited, and may be selected appropriately in accordance with the object. Examples include metals, alloys, metal oxides, electrically conductive compounds, mixtures thereof, and the like. Among these, materials with a work function of 4 eV or more are preferable.

Concrete examples of the material of the positive electrode are electrically conductive metal oxides such as tin oxide, zinc oxide, indium oxide, indium tin oxide (ITO), and the like; metals such as gold, silver, chromium, nickel, or the like; mixtures or layered structures of these metals and electrically conductive metal oxides; inorganic electrically conductive substances such as copper iodide, copper sulfide, and the like; organic electrically conductive materials such as polyaniline, polythiophene, polypyrrol, and the like; layered structures of these materials and ITO; and the like. A single one of these materials may be used, or two or more materials may be used in combination. Among these, electrically conductive metal oxides are preferable, and ITO is particularly preferable from the standpoints of produceability, high conductivity, transparency, and the like.

The thickness of the positive electrode is not particularly limited, and can be appropriately selected in accordance with the material and the like. However, a thickness of 1 to 5000 nm is preferable, and a thickness of 20 to 200 nm is more preferable.

The positive electrode is usually formed on a substrate formed of a glass such as soda lime glass, non-alkali glass or the like; a transparent resin; or the like.

When a glass is used as the substrate, a non-alkali glass, or a soda lime glass which has been subjected to barrier coating treatment with silica or the like, is preferable from the standpoint of few eluted ions from the glass.

The thickness of the substrate is not particularly limited provided that it is thickness sufficient to maintain the mechanical strength. When a glass is used as the substrate, the thickness is usually 0.2 mm or more, and 0.7 mm or more is preferable.

The positive electrode can be suitably formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, a method of coating a dispersion of ITO by a chemical reaction method (a sol-gel method or the like), or the like.

By carrying out washing or other processings on the positive electrode, the driving voltage of the organic EL element can be lowered, and the light-emitting efficiency can be increased. Suitable examples of the other processings include, in the case in which the material of the positive electrode is ITO for example, UV-ozone processing, plasma processing, or the like.

—Negative Electrode—

The negative electrode is not particularly limited, and can be appropriately selected in accordance with the object. The negative electrode preferably can supply electrons to the organic thin-film layer. Specifically, when the organic thin-film layer has only the light-emitting layer, it is preferable that the negative electrode can supply electrons to the light-emitting layer. When the organic thin-film layer also has an electron transporting layer, it is preferable that the negative electrode can supply electrons to the electron transporting layer. When there is an electron injecting layer between the organic thin-film layer and the negative electrode, it is preferable that the negative electrode can supply electrons to the electron injecting layer.

The material of the negative electrode is not particularly limited, and can be appropriately selected in accordance with the adhesion between the negative electrode and the layers or molecules adjacent thereto such as the electron transporting layer, the light-emitting layer, and the like, the ionization potential, the stability, and the like. Examples are metals, alloys, metal oxides, electrically conductive compounds, mixtures thereof, and the like.

Specific examples of the material of the negative electrode are alkali metals (e.g., Li, Na, K, Cs, and the like), alkaline earth metals (e.g., Mg, Ca, and the like), gold, silver, lead, aluminum, sodium-potassium alloys or mixed metals thereof, lithium-aluminum alloys or mixed metals thereof, magnesium-silver alloys or mixed metals thereof, rare earth metals such as indium, ytterbium, or the like, alloys thereof, and the like.

A single type of these materials may be used, or a combination of two or more types may be used. Among these, materials having a work function of 4 eV or less are preferable. Aluminum, lithium-aluminum alloys or mixed metals thereof, magnesium-silver alloys or mixed metals thereof, and the like are more preferable.

The thickness of the negative electrode is not particularly limited, and may be appropriately selected in accordance with the material of the negative electrode or the like. The thickness is preferably 1 to 10,000 nm, and 20 to 200 nm is more preferable.

The negative electrode can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

When two or more types of materials are used in combination as the material of the negative electrode, the two or more types of materials may be vapor deposited simultaneously such that an alloy electrode or the like is formed, or an alloy which is prepared in advance may be vapor deposited such that an alloy electrode or the like is formed.

For the values of resistance of the positive electrode and the negative electrode, lower values are preferable. It is preferable that the values of resistance are several hundred Ω/□ or less.

—Positive Hole Injecting Layer—

The positive hole injecting layer is not particularly limited, and may be appropriately selected in accordance with the object. For example, it is preferable that the positive hole injecting layer has the function of injecting positive holes from the positive electrode at the time when an electrical field is applied.

The material of the positive hole injecting layer is not particularly limited, and may be appropriately selected in accordance with the object. Suitable examples include copper phthalocyanine, polyaniline, starburst amine expressed by the following formula, and the like.

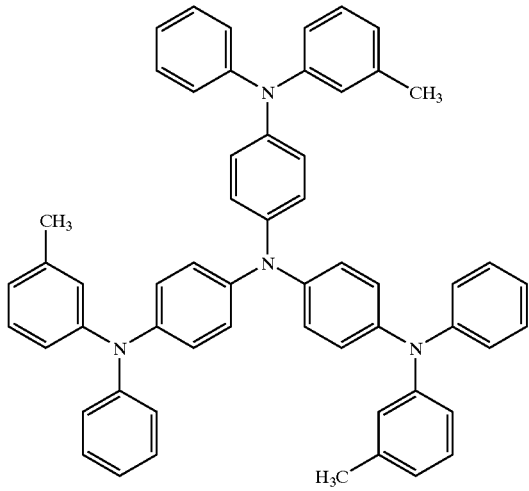

The thickness of the positive hole injecting layer is not particularly limited, and may be appropriately selected in accordance with the object. For example, a thickness of about 1 to 100 nm is preferable, and 5 to 50 nm is more preferable.

The positive hole injecting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Positive Hole Transporting Layer—

The positive hole transporting layer is not particularly limited, and may be appropriately selected in accordance with the object. For example, a layer which has either a function of transporting positive holes from the positive electrode at the time when an electrical field is applied, or a function of blocking electrons which are injected from the negative electrode, is preferable.

As described above, the condensed eight-ring aromatic compound may be used as the material of the positive hole transporting layer. Materials other than the condensed eight-ring aromatic compound are not particularly limited and may be appropriately selected in accordance with the object. Examples include aromatic amine compounds, carbazole, imidazole, triazole, oxazole, oxadiazole, polyaryl alkane, pyrazoline, pyrazolone, phenylene diamine, aryl amine, amine-substituted chalcone, styryl anthracene, fluorenon, hydrazone, stilbene, silazane, styryl amine, aromatic dimethylidine compound, porphin compounds, polysilane compounds, poly(N-vinylcarbazole), aniline copolymers, thiophene oligomers and polymers, electrically conductive macromolecular oligomers and polymers such as polythiophene and the like, carbon film, and the like.

A single one of these substances can be used, or two or more types may be used in combination. Among these, aromatic amine compounds are preferable, and specifically TPD (N,N'-diphenyl-N,N'-bis(3-methylphenyl)-[1,1'-biphenyl]-4,4'-diamine) represented by the following formula, and NPD (N,N'-dinaphthyl-N,N'-diphenyl-[1,1'-biphenyl]-4,4'-diamine) represented by the following formula, and the like are more preferable.

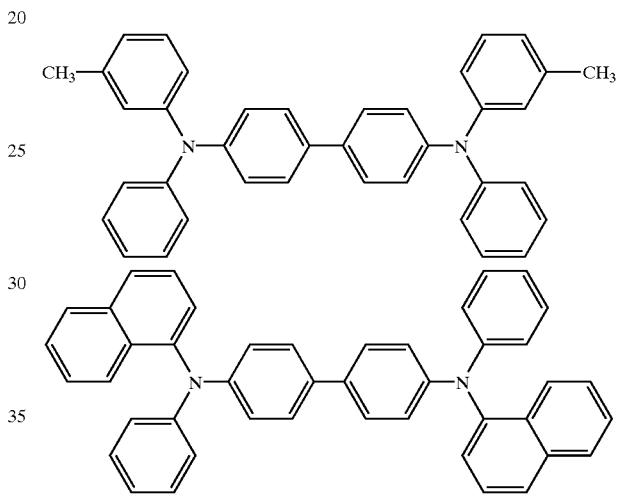

The thickness of the positive hole transporting layer is not particularly limited, and may be appropriately selected in accordance with the object. The thickness is usually 1 to 500 nm, and a thickness of 10 to 100 nm is preferable.

The positive hole transporting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Electron Transporting Layer—

The electron transporting layer is not particularly limited, and may be appropriately selected in accordance with the object. For example, a layer which has either a function of transporting electrons from the negative electrode, or a function of blocking positive holes which are injected from the positive electrode, is preferable.

As described above, the condensed eight-ring aromatic compound may be used as the material of the electron transporting layer. Materials other than the condensed eight-ring aromatic compound are not particularly limited and may be appropriately selected in accordance with the object. Examples include quinoline derivatives of organic metal complexes or the like whose ligands are 8-quinolinols such as tris(8-quinolinolato)aluminum (Alq) or derivatives thereof, oxadiazole derivatives, triazole derivatives, phenanthroline derivatives, perylene derivatives, pyridine derivatives, pyrimidine derivatives, quinoxaline derivatives, diphenylquinone derivatives, nitro-substituted fluorene derivatives, and the like.

The thickness of the electron transporting layer is not particularly limited, and may be appropriately selected in accordance with the object. The thickness is usually around 1 to 500 nm, and 10 to 50 nm is preferable.

The electron transporting layer may be a single-layer structure, or may be a laminated layer structure.

The electron transporting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Other Layers—

The organic EL element of the present invention may have other layers which are appropriately selected in accordance with the object. Suitable examples of other layers are a protective layer and the like.

The protective layer is not particularly limited, and may be appropriately selected in accordance with the object. For example, a layer which can suppress the penetration, into the organic EL element, of molecules and substances which promote deterioration of the organic EL element, such as moisture, oxygen, and the like, is preferable.

Examples of the material of the protective layer are metals such as In, Sn, Pb, Au, Cu, Ag, Al, Ti, Ni, and the like, metal oxides such as MgO, SiO, $SiO_2$, $Al_2O_3$, GeO, NiO, CaO, BaO, $Fe_2O_3$, $Y_2O_3$, $TiO_2$, and the like, nitrides such as SiN, $SiN_xO_y$, and the like, metal fluorides such as $MgF_2$, LiF, $AlF_3$, $CaF_2$, and the like, polyethylene, polypropylene, polymethylmethacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing a monomer mixture containing tetrafluoroethylene and at least one type of co-monomer, fluorine-containing copolymers having a cyclic structure in the copolymerized main chain, water-absorbent substances whose coefficient of water absorption is 1% or more, moisture-proof substances whose coefficient of water absorption is 0.1% or less, and the like.

The protective layer can suitably be formed by the above-described methods such as, for example, a vapor deposition method, a wet-type film forming method, a sputtering method, a reactive sputtering method, an MBE (molecular beam epitaxy) method, a cluster ion beam method, an ion plating method, a plasma polymerization method (high-frequency excited ion plating method), a printing method, a transfer method, or the like.

The structure of the organic EL element of the present invention is not particularly limited, and may be appropriately selected in accordance with the object. Suitable examples of the layer structure are the following layer structures (1) through (13): (1) positive electrode/positive hole injecting layer/positive hole transporting layer/light-emitting layer/electron transporting layer/electron injecting layer/negative electrode, (2) positive electrode/positive hole injecting layer/positive hole transporting layer/light-emitting layer/electron transporting layer/negative electrode, (3) positive electrode/positive hole transporting layer/light-emitting layer/electron transporting layer/electron injecting layer/negative electrode, (4) positive electrode/positive hole transporting layer/light-emitting layer/electron transporting layer/negative electrode, (5) positive electrode/positive hole injecting layer/positive hole transporting layer/light-emitting and electron transporting layer/electron injecting layer/negative electrode, (6) positive electrode/positive hole injecting layer/positive hole transporting layer/light-emitting and electrode transporting layer/negative electrode, (7) positive electrode/positive hole transporting layer/light-emitting and electron transporting layer/electron injecting layer/negative electrode, (8) positive electrode/positive hole transporting layer/light-emitting and electron transporting layer/negative electrode, (9) positive electrode/positive hole injecting layer/positive hole transporting and light-emitting layer/electron transporting layer/electron injecting layer/negative electrode, (10) positive electrode/positive hole injecting layer/positive hole transporting and light-emitting layer/electron transporting layer/negative electrode, (11) positive electrode/positive hole transporting and light-emitting layer/electron transporting layer electron injecting layer/negative electrode, (12) positive electrode/positive hole transporting and light-emitting layer/electron transporting layer/negative electrode, (13) positive electrode/positive hole transporting and light-emitting and electron transporting layer/negative electrode, and the like.

Among these layer structures, when (4) positive electrode/positive hole transporting layer/light-emitting layer/electron transporting layer/negative electrode is illustrated, it is as in FIG. 1. An organic EL element 10 has a layer structure in which a positive electrode 14 (e.g., an ITO electrode) formed on a glass substrate 12, a positive hole transporting layer 16, a light-emitting layer 18, an electron transporting layer 20, and a negative electrode 22 (e.g., an Al—Li electrode) are layered in that order. The positive electrode 14 (e.g., an ITO electrode) and the negative electrode 22 (e.g., an Al—Li electrode) are connected to each other via a power source. An organic thin-film layer 24 for emitting red light is formed by the positive hole transporting layer 16, the light-emitting layer 18, and the electron transporting layer 20.

As the emission wavelength of the organic EL element of the present invention, 580 to 780 nm is preferable, and 600 to 650 nm is more preferable.

With regard to the light-emitting efficiency of the organic EL element of the present invention, the organic EL element desirably emits red light at a voltage of 10V or less, and preferably emits red light at 7V or less, and more preferably emits red light at 5V or less.

At an applied voltage of 10V, the light-emitting luminance of the organic EL element of the present invention is preferably 100 $cd/m^2$ or more, and is more preferably 500 $cd/m^2$ or more, and is particularly preferably 1000 $cd/m^2$ or more.

The organic EL element of the present invention can be suitably used in various types of fields such as, for example, computers, vehicle-mounted display devices, outdoor display devices, machines for household use, machines for industrial use, machines for home electronics, traffic-related display devices, clock display devices, calendar display devices, luminescent screens, sound machines, and the like. The organic EL element of the present invention can particularly preferably be used in the organic EL display of the present invention which will be described hereinafter.

<Organic EL Display>

The organic EL display of the present invention is not particularly limited, other than that it utilizes the organic EL element of the present invention, and can appropriately utilize known structures.

The organic EL display of the present invention may emit only light of the single color of red, or may be a full-color type display which emits lights of multiple colors.

As methods for making the organic EL display a full-color type display, for example, as disclosed in "Gekkan Display", September 2000, pp. 33–37, there are a three-color light-emitting method in which organic EL elements, which emit lights corresponding to the three primary colors (blue (B), green (G), red (R)), respectively, are disposed on a substrate; a white color method in which white light emitted by an organic EL element for emitting white light is passed through a color filter so as to be divided into the three primary colors; a color conversion method in which blue light emitted by an organic EL element for emitting blue light is passed through a fluorescent dye layer and converted into red (R) and green (G); and the like. However, because the organic EL element of the present invention which is used is for emitting red light, the present invention can particularly suitably utilize the three-color light-emitting method.

When manufacturing a full-color type organic EL display by the three-color light-emitting method, in addition to the organic EL element of the present invention which is for emitting red light, an organic EL element for emitting green light and an organic EL element for emitting blue light are needed.

The organic EL element for emitting green light is not particularly limited, and can be appropriately selected from among known elements. For example, an element whose layer structure is ITO (positive electrode)/NPD/Alq/Al—Li (negative electrode), or the like is suitable.

The organic EL element for emitting blue light is not particularly limited, and can be appropriately selected from among known elements. For example, an element whose layer structure is ITO (positive electrode)/NPD/DPVBi expressed by the following formula/Alq/Al—Li (negative electrode), or the like is suitable. DPVBi is 4,4'-bis(2,2'-diphenyl-ethane-1-yl)-biphenyl.

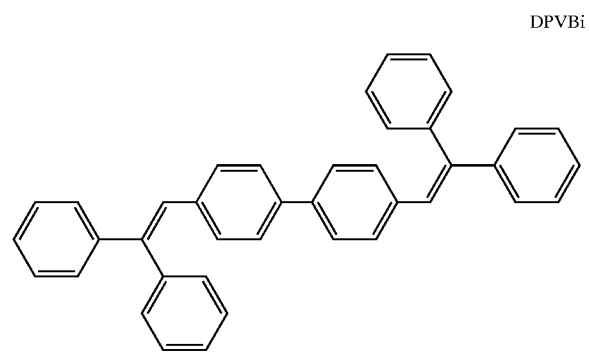

DPVBi

The mode of the organic EL display is not particularly limited, and can be appropriately selected in accordance with the object. Suitable examples include a passive matrix panel, an active matrix panel, and the like, such as those disclosed in "Nikkei Electronics", No. 765, Mar. 13, 2000, pp. 55–62.

Figure 2:
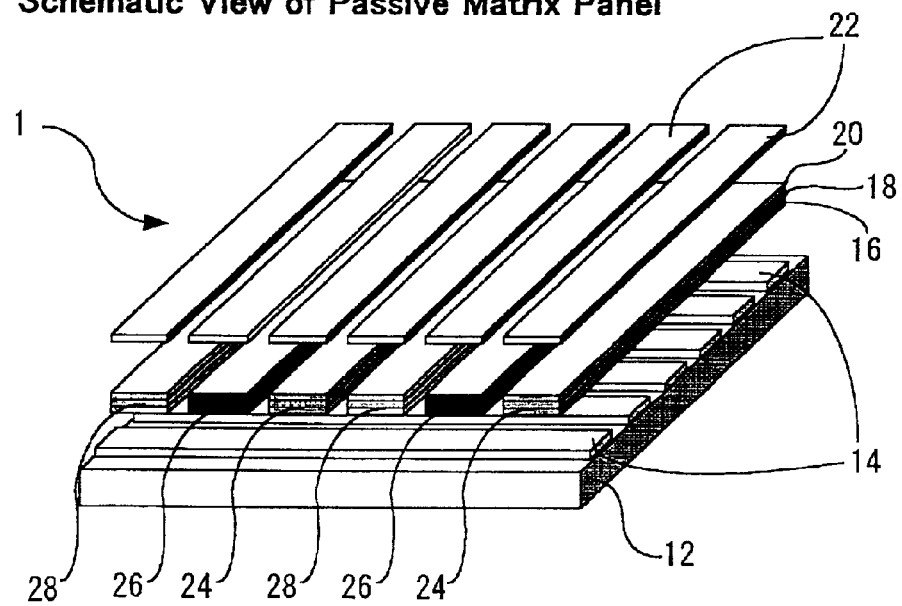
FIG. 2 is a schematic explanatory view for explaining a structural example of a passive matrix type organic EL display (passive matrix panel).

The passive matrix panel has, as shown in FIG. 2 for example, the strip-shaped positive electrodes 14 (e.g., ITO electrodes), which are disposed in parallel, on the glass substrate 12. The passive matrix panel has, on the positive electrodes 14, the strip-shaped organic thin-film layers 24 for emitting red light, strip-shaped organic thin-film layers 26 for emitting green light, and strip-shaped organic thin-film layers 28 for emitting blue light, which are disposed in order and parallel to each other and in a direction substantially orthogonal to the positive electrodes 14. The passive matrix panel has, on the organic thin-film layers 24 for emitting red light, the organic thin-film layers 26 for emitting green light, and the organic thin-film layers 28 for emitting blue light, the negative electrodes 22 having the same configurations as the organic thin-film layers 24, 26, 28.

Figure 3:
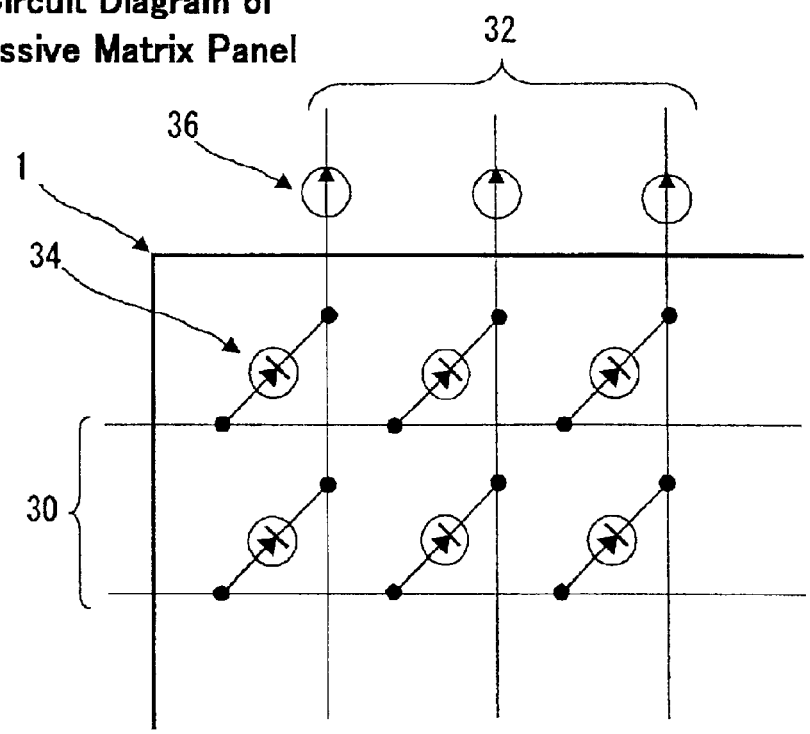
FIG. 3 is a schematic explanatory view for explaining circuits in the passive matrix type organic EL display (passive matrix panel) shown in FIG. 2.

At the passive matrix panel, as shown in FIG. 3 for example, a positive electrode line 30 formed from a plurality of the positive electrodes 14, and a negative electrode line 32 formed from a plurality of the negative electrodes 22, intersect one another in substantially orthogonal directions so as to form a circuit. The respective organic thin-film layers 24, 26, 28 for emitting red light, green light, and blue light, which are positioned at the respective points of intersection, function as pixels. A plurality of organic EL elements 34 exist in correspondence with the respective pixels. At the passive matrix panel, when current is applied by a constant current source 36 to one of the positive electrodes 14 in the positive electrode line 30 and one of the negative electrodes 22 in the negative electrode line 32, at that time, current is applied to the organic EL thin-film layer which is positioned at that point of intersection, and the organic EL thin-film layer at that position emits light. By controlling the emission of light of the pixel units, a full-color image can easily be formed.

Figure 4:
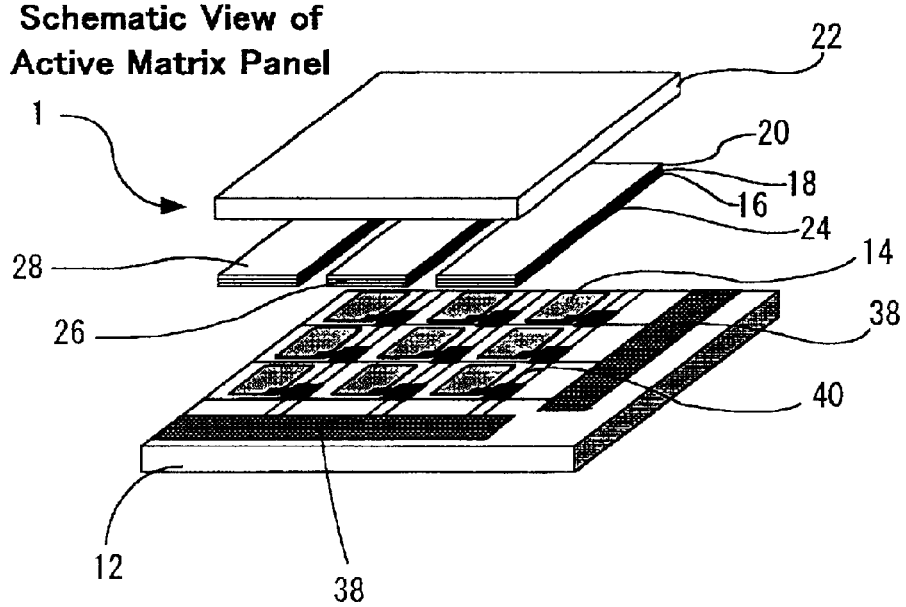
FIG. 4 is a schematic explanatory view for explaining a structural example of an active matrix type organic EL display (active matrix panel).

As shown in FIG. 4 for example, in the active matrix panel, scan lines, data lines, and current supplying lines are formed in a gridiron layout on the glass substrate 12. The active matrix panel has TFT circuits 40, which are connected to the scan lines and the like forming the gridiron layout and which are disposed in the respective squares of the grid, and the positive electrodes 14 (e.g., ITO electrodes) which can be driven by the TFT circuits 40 and which are disposed within the respective grids. The active matrix panel has, on the positive electrodes 14, the strip-shaped organic thin-film layers 24 for emitting red light, the strip-shaped organic thin-film layers 26 for emitting green light, and the strip-shaped organic thin-film layers 28 for emitting blue light, which are disposed in order and parallel to each other. The active matrix panel has, on the organic thin-film layers 24 for emitting red light, the organic thin-film layers 26 for emitting green light, and the organic thin-film layers 28 for emitting blue light, the negative electrode 22 which is disposed so as to cover all of the organic thin-film layers 24, 26, 28. The organic thin-film layers 24 for emitting red light, the organic thin-film layers 26 for emitting green light, and the organic thin-film layers 28 for emitting blue light each have the positive hole transporting layer 16, the light-emitting layer 18, and the electron transporting layer 20.

Figure 5:
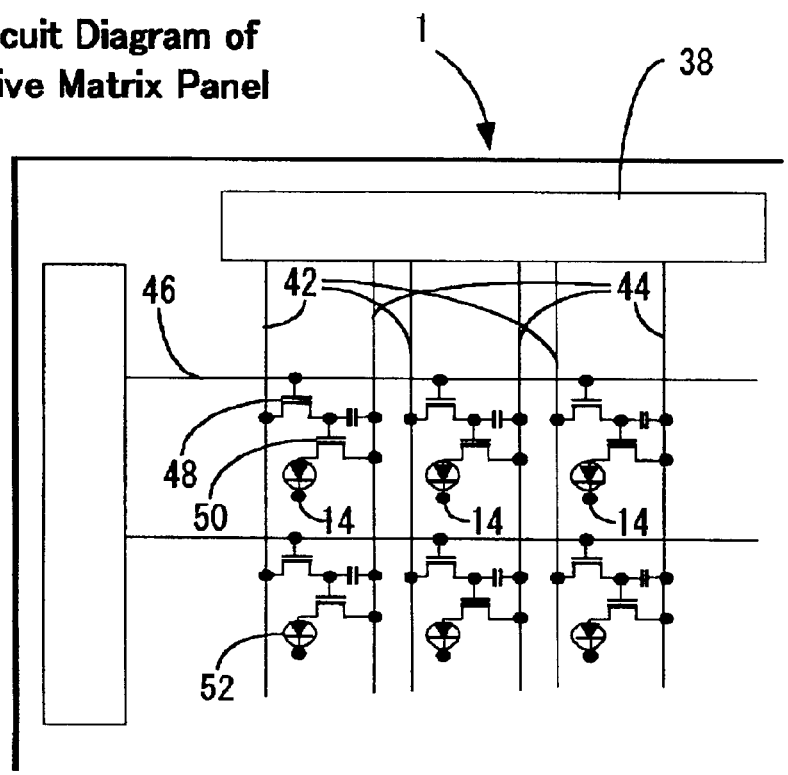
FIG. 5 is a schematic explanatory view for explaining circuits in the active matrix type organic EL display (active matrix panel) shown in FIG. 4.

In the active matrix panel, as shown in FIG. 5 for example, a plurality of scan lines 46 which are provided parallel, and a plurality of data lines 42 and current supplying lines which are provided parallel, are orthogonal to one another so as to form a gridiron layout. A TFT 48 for switching and a TFT 50 for driving are connected to form a circuit in each square of the gridiron. When current is applied from a driving circuit 38, the TFT 48 for switching and the TFT 50 for driving can be driven per square of the gridiron. In each square of the gridiron, the organic thin-film layers 24, 26, 28 for emitting red light, green light and blue light function as pixels. At the active matrix panel, when voltage is applied from the driving circuit 38 to one of the scan lines 46 disposed in the lateral direction and the current supplying line 44 disposed in the lengthwise direction, at that time, the TFT 48 for switching which is positioned at that point of intersection is driven, and accompanying this driving, the TFT 50 for driving is driven, and an organic EL element 52 at that position emits light. By controlling the emission of light of the pixel units, a full-color image can easily be formed.

The organic EL display of the present invention can be suitably used in various types of fields such as, for example, computers, vehicle-mounted display devices, outdoor display devices, machines for household use, machines for industrial use, machines for home electronics, traffic-related display devices, clock display devices, calendar display devices, luminescent screens, sound machines, and the like.

EXAMPLES

Hereinafter, Examples of the present invention will be concretely described. However, the present invention is not to be limited in any way to these Examples.

Synthesis Example 1

Synthesis of dinaphtho(2':3'-3:4) (2":3"-8:9)pyrene

Dinaphtho (2':3'-3:4) (2":3"-8:9)pyrene represented by the following formula is synthesized in accordance with a publication ("Journal of the Chemical Society", 1949, p. 2013).

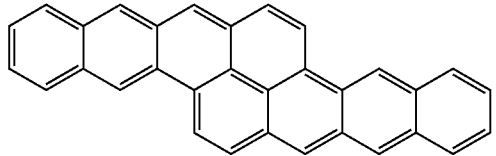

Synthesis Example 2

Synthesis of 5,10-diphenyl-dinaphtho(2':3'-3:4)(2":3"-8:9)pyrene

Dinaphtho(2':3'-3:4)(2":3"-8:9)pyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,10-dibromodinaphtho(2':3'-3:4) (2":3"-8:9)pyrene is obtained. 2 mol equivalent of phenylboronic acid [Ph—B(OH)$_2$] (where "Ph" represents a phenyl group) is refluxed and reacted for two hours with the 5,10-dibromodinaphtho(2':3'-3:4)(2":3"-8:9)pyrene obtained in this way, in a xylene/2M sodium carbonate aqueous solution, by using 0.01 mol equivalent of tetraquis(triphenylphosphine) palladium (0) [Pd(PPh$_3$)$_4$] (where "Ph" represents a phenyl group) as a catalyst. Thereafter, the resultant mixture is purified in accordance with a usual method, and the 5,10-diphenyl-dinaphtho(2':3'-3:4)(2":3"-8:9)pyrene expressed by the following formula is synthesized. (Note that, in the formula, "Ph" represents a phenyl group.)

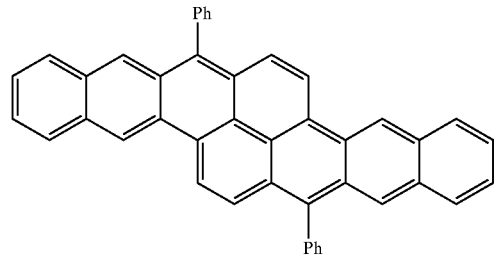

Synthesis Example 3

Synthesis of 5,10-bis(phenylamino)dinaphtho(2':3'-3:4)(2":3"-8:9)pyrene

Dinaphtho(2':3'-3:4)(2":3"-8:9)pyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,10-dibromodinaphtho(2':3'-3:4)(2":3"-8:9)pyrene is obtained. Phenylamine, potassium carbonate, and copper powder are added to the 5,10-dibromodinaphtho(2':3'-3:4)(2":3"-8:9)pyrene obtained in this way, and the mixture is reacted for 30 hours at 200° C. After the reaction solution is diluted with water, the reactant is eluted with chloroform. Thereafter, the resultant substance is purified in accordance with a usual method, and the 5,10-bis(phenylamino)dinaphtho(2':3'-3:4)(2":3"-8:9)pyrene represented by the following formula is synthesized. (Note that, in the formula, "Ph" represents a phenyl group.)

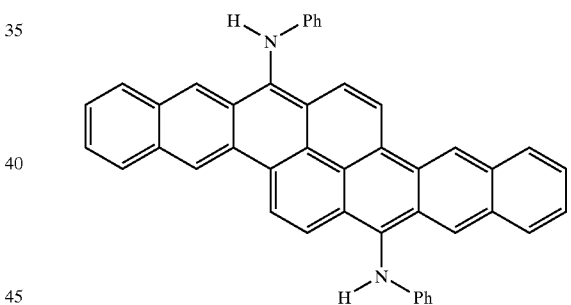

Synthesis Example 4

Synthesis of 5,10-bis(diphenylamino)dinaphtho(2':3'-3:4)(2":3"-8:9)pyrene

Dinaphthopyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,10-dibromodinaphthopyrene is obtained. Diphenylamine, potassium carbonate, and copper powder are added to the 5,10-dibromodinaphtho(2':3'-3:4)(2":3"-8:9)pyrene obtained in this way, and the mixture is reacted for 30 hours at 200° C. After the reaction solution is diluted with water, the reactant is eluted with chloroform. Thereafter, the resultant substance is purified in accordance with a usual method, and the 5,10-bis(diphenylamino)dinaphtho(2':3'-3:4)(2":3"-8:9)pyrene represented by the following formula is synthesized. (Note that, in the formula, "Ph" represents a phenyl group.)

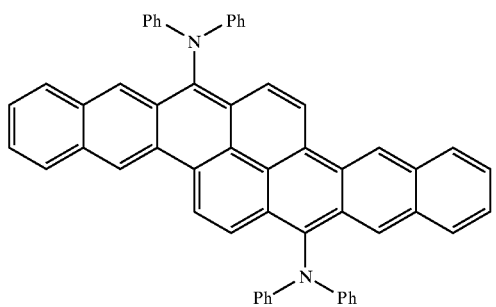

Example 1

A laminated-type organic EL element using dinaphtho(2':3'-3:4)(2":3"-8:9)pyrene in the light-emitting layer is prepared as follows. Namely, a glass substrate, on which ITO electrodes are formed as positive electrodes, is washed with water, acetone and isopropyl alcohol. Using a vacuum vapor deposition device (degree of vacuum=$1\times10^{-6}$ Torr ($1.3\times10^{-4}$ Pa), substrate temperature=room temperature), TPD serving as a positive hole transporting layer is covered on the ITO electrodes so as to be a thickness of 50 nm. Next, a light-emitting layer having a thickness of 20 nm is formed simultaneously by vapor depositing, on the positive hole transporting layer formed by the TPD, dinaphtho(2':3'-3:4)(2":3"-8:9)pyrene and Alq such that the Alq is 99 molecules (99 mol) to 1 molecule (1 mol) of the dinaphtho(2':3'-3:4)(2":3"-8:9)pyrene. Then, Alq serving as an electron transporting layer is covered so as to be a thickness of 30 nm on the light-emitting layer. Then, an Al—Li alloy (Li content=0.5% by mass) serving as the negative electrodes is vapor deposited so as to be a thickness of 50 nm on the electron transporting layer formed by the Alq. The organic EL element is thus prepared.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 980 cd/m² and whose peak is a wavelength of 600 nm, is observed.

Example 2

An organic EL element is prepared in the same way as in Example 1, except that the light-emitting layer is formed simultaneously by vapor depositing dinaphtho(2':3'-3:4)(2":3"-8:9)pyrene, Alq, and rubrene such that the Alq is 94 molecules (94 mol) and the rubrene is 5 molecules (5 mol) to 1 molecule (1 mol) of the dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1500 cd/m² and whose peak is a wavelength of 600 nm, is observed.

Example 3

An organic EL element is prepared in the same way as in Example 1, except that the dinaphtho(2':3'-3:4)(2":3"-8:9) pyrene in Example 1 is replaced with 5,10-diphenyl-dinaphtho(2':3'-3:4) (2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1390 cd/m² and whose peak is a wavelength of 630 nm, is observed.

Example 4

An organic EL element is prepared in the same way as in Example 2, except that the dinaphtho(2':3'-3:4)(2":3"-8:9) pyrene in Example 2 is replaced with 5,10-diphenyl-dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 2010 cd/m² and whose peak is a wavelength of 630 nm, is observed.

Example 5

An organic EL element is prepared in the same way as in Example 1, except that the dinaphtho(2':3'-3:4)(2":3"-8:9) pyrene in Example 1 is replaced with 5,10-bis(phenylamino)dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1260 cd/m² and whose peak is a wavelength of 650 nm, is observed.

Example 6

An organic EL element is prepared in the same way as in Example 2, except that the dinaphtho(2':3'-3:4)(2":3"-8:9) pyrene in Example 2 is replaced with 5,10-bis(phenylamino)dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1700 cd/m² and whose peak is a wavelength of 650 nm, is observed.

Example 7

An organic EL element is prepared in the same way as in Example 1, except that the dinaphtho(2':3'-3:4)(2":3"-8:9) pyrene in Example 1 is replaced with 5,10-bis(diphenylamino)dinaphtho(2':3'-3:4)(2":3"-8:9)pyrene, and Alq is not used in the light-emitting layer, and the thickness of the electron transporting layer is made to be 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 650 cd/m² and whose peak is a wavelength of 655 nm, is observed.

Example 8

An organic EL element is prepared in the same way as in Example 1, except that the dinaphtho(2':3'-3:4)(2":3"-8:9)

pyrene in Example 1 is replaced with 5,10-bis(diphenylamino)dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1300 cd/m$^2$ and whose peak is a wavelength of 655 nm, is observed.

Example 9

An organic EL element is prepared in the same way as in Example 2, except that the dinaphtho(2':3'-3:4)(2":3"-8:9) pyrene in Example 2 is replaced with 5,10-bis(diphenylamino)dinaphtho(2':3'-3:4)(2":3"-8:9)pyrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1820 cd/m$^2$ and whose peak is a wavelength of 655 nm, is observed.

Example 10

An organic EL element is prepared in the same way as in Example 1, except that the dinaphtho(2':3'-3:4)(2":3"-8:9) pyrene in Example 1 is replaced with 5,10-bis(diphenylamino)dinaphtho(2':3'-3:4)(2":3"-8:9)pyrene, and the positive hole transporting layer is not formed, and the light-emitting layer is made to be a positive hole transporting and light-emitting layer having a thickness of 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 380 cd/m$^2$ and whose peak is a wavelength of 655 nm, is observed.

Example 11

An organic EL element is prepared in the same way as in Example 1, except that the dinaphtho(2':3'-3:4)(2":3"-8:9) pyrene in Example 1 is replaced with 5,10-diphenyl-dinaphtho(2':3'-3:4)(2":3"-8:9)pyrene, and the electron transporting layer is not formed, and the light-emitting layer is made to be an electron transporting and light-emitting layer having a thickness of 30 nm.

When voltage is applied to the ITO electrodes (positive electrodes) and the Al—Li alloy (negative electrodes) of the prepared organic EL element, the emission of red light at a voltage of 7V or more is observed in the organic EL element. At an applied voltage of 10V, the emission of red light, whose light-emitting luminance is 160 cd/m$^2$ and whose peak is a wavelength of 630 nm, is observed.

Synthesis Example 5
Synthesis of Dibenzanthanthrene

Dibenzanthanthrene expressed by the following formula is synthesized in accordance with a publication ("Bericht", No. 76, p. 329 (1943)).

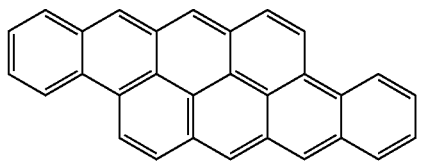

Synthesis Example 6

Synthesis of 7,15-diphenyl-dibenzanthanthrene

Dibenzanthanthrene is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 7,15-dibromodibenzanthanthrene is obtained. 2 mol equivalent of phenylboronic acid [Ph—B(OH)$_2$] (wherein "Ph" represents a phenyl group) is refluxed and reacted for twelve hours with the 7,15-dibromodibenzanthanthrene obtained in this way, in a xylene/2M sodium carbonate aqueous solution, by using 0.01 mol equivalent of tetraquis(triphenylphosphine) palladium (0) [Pd(PPh$_3$)$_4$] (where "Ph" represents a phenyl group) as a catalyst. Thereafter, the resultant mixture is purified in accordance with a usual method, and the 7,15-diphenyl-dibenzanthanthrene expressed by the following formula is synthesized. (Note that, in the formula, "Ph" represents a phenyl group.)

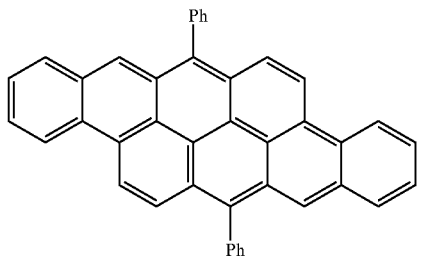

Synthesis Example 7

Synthesis of 7,15-bis(phenylamino)dibenzanthanthrene

Dibenzanthanthrene is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 7,15-dibromodibenzanthanthrene is obtained. Phenylamine, potassium carbonate, and copper powder are added to the 7,15-dibromodibenzanthanthrene obtained in this way, and the mixture is reacted for 30 hours at 200° C. After the reaction solution is diluted with water, the reactant is eluted with chloroform. Thereafter, the resultant substance is purified in accordance with a usual method, and the 7,15-bis(phenylamino)dibenzanthanthrene represented by the following formula is synthesized. (Note that, in the formula, "Ph" represents a phenyl group.)

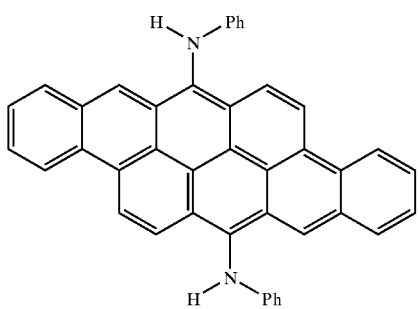

Synthesis Example 8
Synthesis of 7,15-bis(diphenylamino)dibenzanthanthrene

Dibenzanthanthrene is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 7,15-dibromodibenzanthanthrene is obtained. Diphenylamine, potassium carbonate, and copper powder are added to the 7,15-dibromodibenzanthanthrene obtained in this way, and the mixture is reacted for 30 hours at 200° C. After the reaction solution is diluted with water, the reactant is eluted with chloroform. Thereafter, the resultant substance is purified in accordance with a usual method, and the 7,15-bis(diphenylamino)dibenzanthanthrene represented by the following formula is synthesized. (Note that, in the formula, "Ph" represents a phenyl group.)

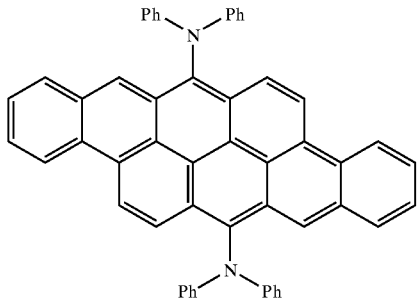

Example 12

A laminated-type organic EL element using dibenzanthanthrene in the light-emitting layer is prepared as follows. Namely, a glass substrate, on which ITO electrodes are formed as positive electrodes, is washed with water, acetone and isopropyl alcohol. Using a vacuum vapor deposition device (degree of vacuum=$1\times10^{-6}$ Torr ($1.3\times10^{-4}$ Pa), substrate temperature=room temperature), TPD serving as a positive hole transporting layer is covered on the ITO electrodes so as to be a thickness of 50 nm. Next, a light-emitting layer having a thickness of 20 nm is formed by simultaneous vapor depositing, on the positive hole transporting layer formed by the TPD, dibenzanthanthrene and Alq such that the Alq is 99 molecules (99 mol) to 1 molecule (1 mol) of the dibenzanthanthrene. Then, Alq serving as an electron transporting layer is covered so as to be a thickness of 30 nm on the light-emitting layer. Then, an Al—Li alloy (Li content=0.5% by mass) serving as the negative electrodes is vapor deposited so as to be a thickness of 50 nm on the electron transporting layer formed by the Alq. The organic EL element is thus prepared.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 790 cd/m$^2$ and whose peak is a wavelength of 620 nm, is observed.

Example 13

An organic EL element is prepared in the same way as in Example 12, except that the light-emitting layer is formed by simultaneous vapor depositing dibenzanthanthrene, Alq and rubrene such that the Alq is 94 molecules (94 mol) and the rubrene is 5 molecules (5 mol) with respect to 1 molecule (1 mol) of the dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1380 cd/m$^2$ and whose peak is a wavelength of 620 nm, is observed.

Example 14

An organic EL element is prepared in the same way as in Example 12, except that the dibenzanthanthrene in Example 12 is replaced with 7,15-diphenyl-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1450 cd/m$^2$ and whose peak is a wavelength of 650 nm, is observed.

Example 15

An organic EL element is prepared in the same way as in Example 13, except that the dibenzanthanthrene in Example 13 is replaced with 7,15-diphenyl-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 2240 cd/m$^2$ and whose peak is a wavelength of 650 nm, is observed.

Example 16

An organic EL element is prepared in the same way as in Example 12, except that the dibenzanthanthrene in Example 12 is replaced with 7,15-bis(phenylamino)-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1060 cd/m$^2$ and whose peak is a wavelength of 660 nm, is observed.

Example 17

An organic EL element is prepared in the same way as in Example 13, except that the dibenzanthanthrene in Example 13 is replaced with 7,15-bis(phenylamino)-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1410 cd/m² and whose peak is a wavelength of 660 nm, is observed.

Example 18

An organic EL element is prepared in the same way as in Example 12, except that the dibenzanthanthrene in Example 12 is replaced with 7,15-bis(diphenylamino)-dibenzanthanthrene, Alq is not used in the light-emitting layer, and the thickness of the electron transporting layer is made to be 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 550 cd/m² and whose peak is a wavelength of 670 nm, is observed.

Example 19

An organic EL element is prepared in the same way as in Example 12, except that the dibenzanthanthrene in Example 12 is replaced with 7,15-bis(diphenylamino)-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1100 cd/m² and whose peak is a wavelength of 670 nm, is observed.

Example 20

An organic EL element is prepared in the same way as in Example 13, except that the dibenzanthanthrene in Example 13 is replaced with 7,15-bis(diphenylamino)-dibenzanthanthrene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1410 cd/m² and whose peak is a wavelength of 670 nm, is observed.

Example 21

An organic EL element is prepared in the same way as in Example 12, except that the dibenzanthanthrene in Example 12 is replaced with 7,15-bis(diphenylamino)-dibenzanthanthrene, the positive hole transporting layer is not formed, and the light-emitting layer is made to be a positive hole transporting and light-emitting layer of a thickness of 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 300 cd/m² and whose peak is a wavelength of 670 nm, is observed.

Example 22

An organic EL element is prepared in the same way as in Example 12, except that the dibenzanthanthrene in Example 12 is replaced with 7,15-diphenyl-dibenzanthanthrene, the electron transporting layer is not formed, and the light-emitting layer is made to be an electron transporting and light-emitting layer of a thickness of 30 nm.

When voltage is applied to the ITO electrodes (positive electrodes) and the Al—Li alloy (negative electrodes) of the prepared organic EL element, the emission of red light at a voltage of 7V or more is observed in the organic EL element. At an applied voltage of 10V, the emission of red light, whose light-emitting luminance is 190 cd/m² and whose peak is a wavelength of 650 nm, is observed.

Synthesis Example 9

Synthesis of 6,13-diphenyl-naphthacenonaphthacene

Naphthacenonaphthacene (Chemical Abstract Service (CAS) Registry Number 180-50-1) is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 6,13-dibromonaphthacenonaphthacene is obtained. 2 mol equivalent of phenylboronic acid [Ph—B(OH)₂] (where "Ph" represents a phenyl group) is refluxed and reacted for 12 hours with the 6,13-dibromonaphthacenonaphthacene obtained in this way, in a xylene/2M sodium carbonate aqueous solution, by using 0.01 mol equivalent of tetraquis (triphenylphosphine)palladium (0) [Pd(PPh₃)₄] (where "Ph" represents a phenyl group) as a catalyst. Thereafter, the resultant mixture is purified in accordance with a usual method, and the 6,13-diphenyl-naphthacenonaphthacene expressed by the following formula is synthesized. (Note that, in the formula, "Ph" represents a phenyl group.)

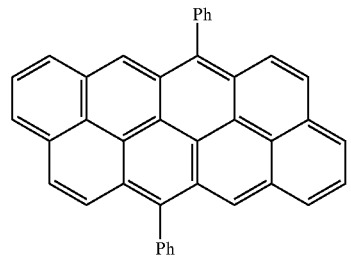

Synthesis Example 10

Synthesis of 6,13-bis(phenylamino)naphthacenonaphthacene

Naphthacenonaphthacene is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 6,13-dibromonaphthacenonaphthacene is obtained. Phenylamine, potassium carbonate, and copper powder are added to the 6,13-dibromonaphthacenonaphthacene obtained in this way, and the mixture is reacted for 30 hours at 200° C. After the reaction solution is diluted with water, the reactant is eluted with chloroform. Thereafter, the resultant substance is purified in accordance with a usual method, and the 6,13-bis (phenylamino)naphthacenonaphthacene represented by the following formula is synthesized. (Note that, in the formula, "Ph" represents a phenyl group.)

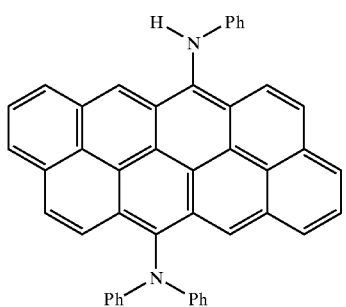

Synthesis Example 11
Synthesis of 6,13-bis(diphenylamino)naphthacenonaphthacene

Naphthacenonaphthacene is dissolved in carbon tetrachloride. While the resultant mixture is cooled, 1 mol equivalent of bromine is added thereto. The mixture is reacted for 4 hours and brominated. Thereafter, the mixture is purified in accordance with a usual method, and 6,13-dibromonaphthacenonaphthacene is obtained. Diphenylamine, potassium carbonate, and copper powder are added to the 6,13-dibromonaphthacenonaphthacene obtained in this way, and the mixture is reacted for 30 hours at 200° C. After the reaction solution is diluted with water, the reactant is eluted with chloroform. Thereafter, the resultant substance is purified in accordance with a usual method, and the 6,13-bis(diphenylamino)naphthacenonaphthacene represented by the following formula is synthesized. (Note that, in the formula, "Ph" represents a phenyl group.)

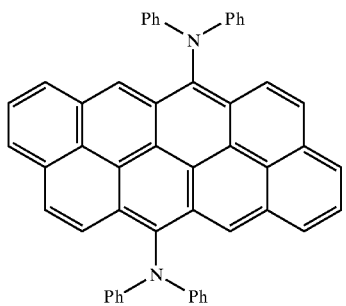

Example 23

A laminated-type organic EL element using naphthacenonaphthacene in the light-emitting layer is prepared as follows. Namely, a glass substrate, on which ITO electrodes are formed as positive electrodes, is washed with water, acetone and isopropyl alcohol. Using a vacuum vapor deposition device (degree of vacuum=$1\times10^{-6}$ Torr ($1.3\times10^{-4}$ Pa), substrate temperature=room temperature), TPD serving as a positive hole transporting layer is covered on the ITO electrodes so as to be a thickness of 50 nm. Next, a light-emitting layer having a thickness of 20 nm is formed by simultaneously vapor depositing, on the positive hole transporting layer formed by the TPD, naphthacenonaphthacene and Alq such that the Alq is 99 molecules (99 mol) to 1 molecule (1 mol) of the naphthacenonaphthacene. Then, Alq serving as an electron transporting layer is covered so as to be a thickness of 30 nm on the light-emitting layer. Then, an Al—Li alloy (Li content=0.5% by mass) serving as the negative electrodes is vapor deposited so as to be a thickness of 50 nm on the electron transporting layer formed by the Alq. The organic EL element is thus prepared.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 820 cd/m$^2$ and whose peak is a wavelength of 600 nm, is observed.

Example 24

An organic EL element is prepared in the same way as in Example 23, except that the light-emitting layer is formed by simultaneously vapor depositing naphthacenonaphthacene, Alq and rubrene such that the Alq is 94 molecules (94 mol) and the rubrene is 5 molecules (5 mol) with respect to 1 molecule (1 mol) of the naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1400 cd/m$^2$ and whose peak is a wavelength of 600 nm, is observed.

Example 25

An organic EL element is prepared in the same way as in Example 23, except that the naphthacenonaphthacene in Example 23 is replaced with 6,13-diphenyl-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1500 cd/m$^2$ and whose peak is a wavelength of 630 nm, is observed.

Example 26

An organic EL element is prepared in the same way as in Example 24, except that the naphthacenonaphthacene in Example 24 is replaced with 6,13-diphenyl-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 2300 cd/m$^2$ and whose peak is a wavelength of 630 nm, is observed.

Example 27

An organic EL element is prepared in the same way as in Example 23, except that the naphthacenonaphthacene in Example 23 is replaced with 6,13-bis(phenylamino)-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1100 cd/m$^2$ and whose peak is a wavelength of 650 nm, is observed.

Example 28

An organic EL element is prepared in the same way as in Example 24, except that the naphthacenonaphthacene in Example 24 is replaced with 6,13-bis(phenylamino)-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1450 cd/m² and whose peak is a wavelength of 650 nm, is observed.

Example 29

An organic EL element is prepared in the same way as in Example 23, except that the naphthacenonaphthacene in Example 23 is replaced with 6,13-bis(diphenylamino)-naphthacenonaphthacene, and Alq is not used in the light-emitting layer, and the thickness of the electron transporting layer is made to be 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 600 cd/m² and whose peak is a wavelength of 655 nm, is observed.

Example 30

An organic EL element is prepared in the same way as in Example 23, except that the naphthacenonaphthacene in Example 23 is replaced with 6,13-bis(diphenylamino)-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1150 cd/m² and whose peak is a wavelength of 655 nm, is observed.

Example 31

An organic EL element is prepared in the same way as in Example 24, except that the naphthacenonaphthacene in Example 24 is replaced with 6,13-bis(diphenylamino)-naphthacenonaphthacene.

When voltage is applied to the ITO electrodes (positive electrodes) and the Al—Li alloy (negative electrodes) of the prepared organic EL element, the emission of red light at a voltage of 5V or more is observed in the organic EL element. At an applied voltage of 10V, the emission of red light, whose light-emitting luminance is 1450 cd/m² and whose peak is a wavelength of 655 nm, is observed.

Example 32

An organic EL element is prepared in the same way as in Example 23, except that the naphthacenonaphthacene in Example 23 is replaced with 6,13-bis(diphenylamino)-naphthacenonaphthacene, and the positive hole transporting layer is not formed, and the light-emitting layer is made to be a positive hole transporting and light-emitting layer of a thickness of 50 nm.

When voltage is applied to the ITO electrodes (positive electrodes) and the Al—Li alloy (negative electrodes) of the prepared organic EL element, the emission of red light at a voltage of 6V or more is observed in the organic EL element. At an applied voltage of 10V, the emission of red light, whose light-emitting luminance is 320 cd/m² and whose peak is a wavelength of 655 nm, is observed.

Example 33

An organic EL element is prepared in the same way as in Example 23, except that the naphthacenonaphthacene in Example 23 is replaced with 6,13-diphenyl-naphthacenonaphthacene, and the electron transporting layer is not formed, and the light-emitting layer is made to be an electron transporting and light-emitting layer of a thickness of 30 nm.

When voltage is applied to the ITO electrodes (positive electrodes) and the Al—Li alloy (negative electrodes) of the prepared organic EL element, the emission of red light at a voltage of 7V or more is observed in the organic EL element. At an applied voltage of 10V, the emission of red light, whose light-emitting luminance is 220 cd/m² and whose peak is a wavelength of 630 nm, is observed.

In accordance with the present invention, there are provided a condensed eight-ring aromatic compound which overcomes the above-described drawbacks of the prior art and which has high color purity of red light and excellent light-emitting efficiency, light-emitting luminance and the like and which is suitable for an organic EL element, an organic EL element which uses the condensed eight-ring aromatic compound and has high color purity of red light and excellent light-emitting efficiency, light-emitting luminance and the like, and an organic EL display which is high-performance and utilizes the organic EL element.

What is claimed is:

1. A condensed eight-ring aromatic compound, wherein the condensed eight-ring aromatic compound has a point-symmetrical skeleton (excluding such cases in which the regions where substituents can be introduced are all hydrogen atoms), wherein the condensed eight-ring aromatic compound is represented by any of following structural formulas (1) through (3):

Structural Formula (1)

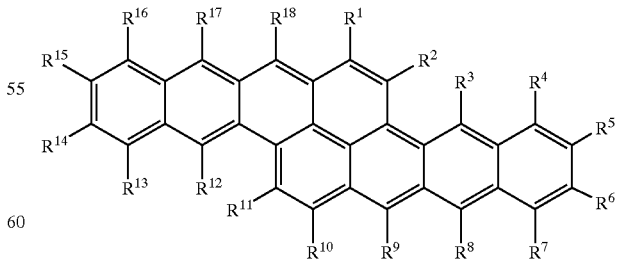

where $R^1$ through $R^{18}$ may be the same or may be different from each other, and represent hydrogen atoms or substituents (excluding cases in which all are hydrogen atoms);

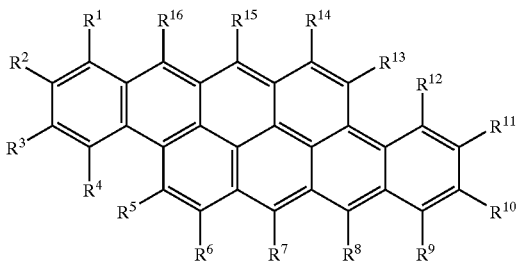

Structural Formula (2)

where $R^1$ through $R^{16}$ may be the same or may be different from each other, and represent hydrogen atoms or substituents (excluding cases in which all are hydrogen atoms);

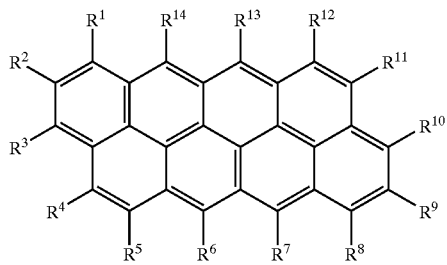

Structural Formula (3)

where $R^1$ through $R^{14}$ may be the same or may be different from each other, and represent hydrogen atoms or substituents (excluding cases in which all are hydrogen atoms).

2. A condensed eight-ring aromatic compound according to claim 1, wherein the substituent is selected from halogen atoms, hydroxy groups, cyano groups, alkyl groups, alkoxy groups, aryl groups, aryloxy groups, arylamino groups, and diarylamino groups.

3. A condensed eight-ring aromatic compound according to claim 1, wherein at least one of $R^1$ through $R^{18}$ in the structural formula (1), at least one of $R^1$ through $R^{16}$ in the structural formula (2), or at least one of $R^1$ through $R^{14}$ in the structural formula (3) is an aryl group.

4. A condensed eight-ring aromatic compound according to claim 1, wherein at least one of $R^1$ through $R^{18}$ in the structural formula (1), at least one of $R^1$ through $R^{16}$ in the structural formula (2), or at least one of $R^1$ through $R^{14}$ in the structural formula (3) is selected from arylamino groups and diarylamino groups.

5. A condensed eight-ring aromatic compound according to claim 1, wherein in structural formula (1), $R^1$ through $R^8$ and $R^{10}$ through $R^{17}$ are hydrogen atoms and $R^9$ and $R^{18}$ are selected from phenyl groups, phenylamino groups, and diphenylamino groups, and in the structural formula (2), $R^1$ through $R^6$, $R^8$ through $R^{14}$, and $R^{16}$ are hydrogen atoms and $R^7$ and $R^{15}$ are selected from phenyl groups, phenylamino groups and diphenylamino groups, or in the structural formula (3), $R^1$ through $R^5$, $R^7$ through $R^{12}$, and $R^{14}$ are hydrogen atoms and $R^6$ and $R^{13}$ are selected from phenyl groups, phenylamino groups and diphenylamino groups.

6. A condensed eight-ring aromatic compound according to claim 1, wherein $R^9$ and $R^{18}$ in structural formula (1), $R^7$ and $R^{15}$ in structural formula (2), or $R^6$ and $R^{13}$ in structural formula (3) are the same.

7. A condensed eight-ring aromatic compound according to claim 1, wherein the condensed eight-ring aromatic compound is contained in an organic EL element.

8. A condensed eight-ring aromatic compound according to claim 3, wherein the condensed eight-ring aromatic compound is contained in at least one of an electron transporting layer and a light-emitting layer of an organic EL element.

9. A condensed eight-ring aromatic compound according to claim 4, wherein the condensed eight-ring aromatic compound is contained in at least one of a positive hole transporting layer and a light-emitting layer of an organic EL element.

10. An organic EL element comprising an organic thin-film layer including a light-emitting layer in between a positive electrode and a negative electrode, and the organic thin-film layer contains a condensed eight-ring aromatic compound, wherein the condensed eight-ring aromatic compound has a point-symmetrical skeleton, wherein the condensed eight-ring aromatic compound is represented by any of following structural formulas (1) through (3):

Structural Formula (1)

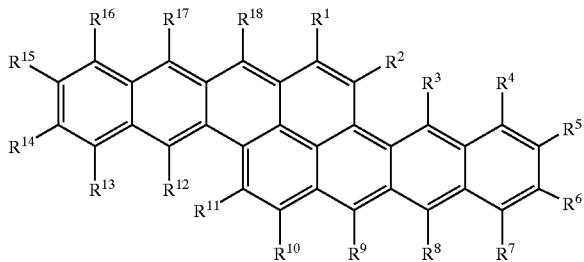

where $R^1$ through $R^{18}$ may be the same or may be different from each other, and represent hydrogen atoms or substituents;

Structural Formula (2)

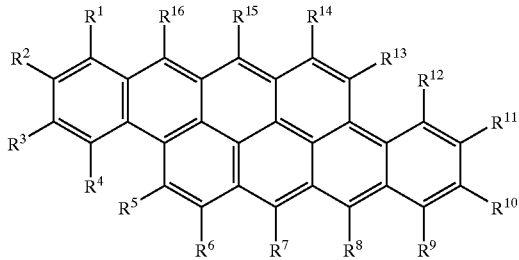

where $R^1$ through $R^{16}$ may be the same or may be different from each other, and represent hydrogen atoms or substituents;

Structural Formula (3)

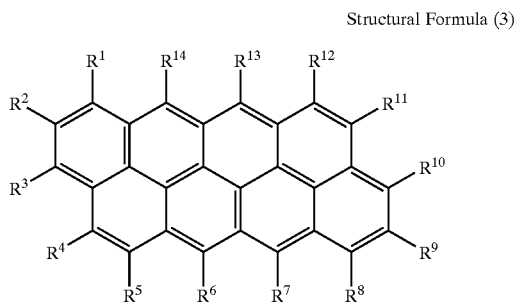

where $R^1$ through $R^{14}$ may be the same or may be different from each other, and represent hydrogen atoms or substituents.

11. An organic EL element according to claim 10, wherein the light-emitting layer contains the condensed eight-ring aromatic compound.

12. An organic EL element according to claim 10, wherein the substituent is selected from halogen atoms, hydroxy groups, cyano groups, alkyl groups, alkoxy groups, aryl groups, aryloxy groups, arylamino groups, and diarylamino groups.

13. An organic EL element according to claim 10, wherein at least one of $R^1$ through $R^{18}$ in the structural formula (1), at least one of $R^1$ through $R^{16}$ in the structural formula (2), or at least one of $R^1$ through $R^{14}$ in the structural formula (3) is an aryl group.

14. An organic EL element according to claim 10, wherein at least one of $R^1$ through $R^{18}$ in the structural formula (1), at least one of $R^1$ through $R^{16}$ in the structural formula (2), or at least one of $R^1$ through $R^{14}$ in the structural formula (3) is an arylamino group.

15. An organic EL element according to claim 10, wherein at least one of $R^1$ through $R^{18}$ in the structural formula (1), at least one of $R^1$ through $R^{16}$ in the structural formula (2), or at least one of $R^1$ through $R^{14}$ in the structural formula (3) is a diarylamino group.

16. An organic EL element according to claim 10, wherein the organic thin-film layer has an electron transporting layer, and the electron transporting layer contains the condensed eight-ring aromatic compound.

17. An organic EL element according to claim 16, wherein at least one of $R^1$ through $R^{18}$ in the condensed eight-ring aromatic compound contained in the electron transporting layer is an aryl group.

18. An organic EL element according to claim 10, wherein the organic thin-film layer has a positive hole transporting layer, and the positive hole transporting layer contains the condensed eight-ring aromatic compound.

19. An organic EL element according to claim 18, wherein at least one of $R^1$ through $R^{18}$ in the condensed eight-ring aromatic compound contained in the positive hole transporting layer is selected from arylamino groups and diarylamino groups.

20. An organic EL element according to claim 10, wherein in the structural formula (1), $R^1$ through $R^8$ and $R^{10}$ through $R^{17}$ are hydrogen atoms and $R^9$ and $R^{18}$ are selected from phenyl groups, phenylamino groups, and diphenylamino groups, and in the structural formula (2), $R^1$ through $R^6$, $R^8$ through $R^{14}$, and $R^{16}$ are hydrogen atoms and $R^7$ and $R^{15}$ are selected from phenyl groups, phenylamino groups and diphenylamino groups, or in the structural formula (3), $R^1$ through $R^5$, $R^7$ through $R^{12}$, and $R^{14}$ are hydrogen atoms and $R^6$ and $R^{13}$ are selected from phenyl groups, phenylamino groups and diphenylamino groups.

21. An organic EL element according to claim 10, wherein $R^9$ and $R^{18}$ in the structural formula (1), $R^7$ and $R^{15}$ in the structural formula (2), or $R^6$ and $R^{13}$ in the structural formula (3) are the same.

22. An organic EL element according to claim 10, wherein the light-emitting layer contains a host compound whose light absorption wavelength is at a short wavelength side of a light absorption wavelength of the condensed eight-ring aromatic compound, and whose light-emitting wavelength is in a vicinity of the light absorption wavelength of the condensed eight-ring aromatic compound.

23. A organic EL element according to claim 10, wherein the light-emitting layer contains n types of host compounds (where n represents an integer of 1 or more), and given that the n host compounds are a first host compound, a second host compound, . . . , an (n−1) th host compound, and an nth host compound in order from the host compound with the shortest light absorption wavelength, a light-emitting wavelength of the first host compound is in a vicinity of a light absorption wavelength of the second host compound, a light-emitting wavelength of the second host compound is in a vicinity of a light absorption wavelength of a third host compound, . . . , a light-emitting wavelength of the (n−1) th host compound is in a vicinity of a light absorption wavelength of the nth host compound, and a light-emitting wavelength of the nth host compound is in a vicinity of a light absorption wavelength of the condensed eight-ring aromatic compound.

24. An organic EL element according to claim 22, wherein a content of the host compound is 90 mol or more with respect to 1 mol of the condensed eight-ring aromatic compound.

25. An organic EL element according to claim 22, wherein the host compound is an aluminum quinoline complex (Alq) represented by the following structural formula:

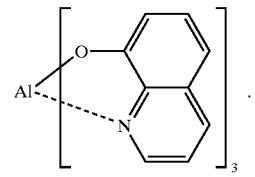

26. An organic EL element according to claim 23, wherein a content of one of the n types of host compounds which has the light-emitting wavelength in the vicinity of the absorption wavelength of the condensed eight-ring aromatic compound, is 1 mol or more with respect to 1 mol of the condensed eight-ring aromatic compound.

27. An organic EL element according to claim 23, wherein the host compounds are an aluminum quinoline complex (Alq) represented by the following structural formula and a rubrene represented by the following structural formula:

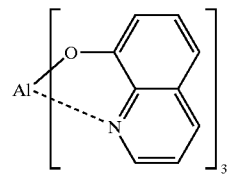

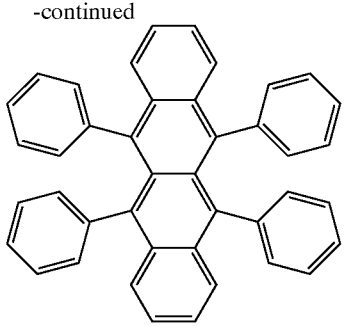

28. An organic EL element according to claim 10, wherein a thickness of the light-emitting layer is 5 to 50 nm.

29. An organic EL element according to claim 10, wherein an emission wavelength is 600 to 650 nm.

30. An organic EL display comprising an organic EL element which comprises an organic thin-film layer including a light-emitting layer in between a positive electrode and a negative electrode, and the organic thin-film layer contains a condensed eight-ring aromatic compound,
   wherein the condensed eight-ring aromatic compound has a point-symmetrical skeleton,
   wherein the condensed eight-ring aromatic compound is represented by any of following structural formulas (1) through (3):

Structural Formula (1)

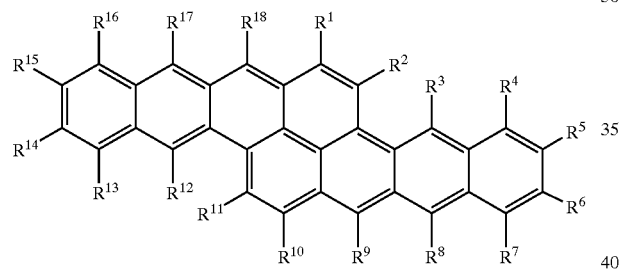

where $R^1$ through $R^{18}$ may be the same or may be different from each other, and represent hydrogen atoms or substituents;

Structural Formula (2)

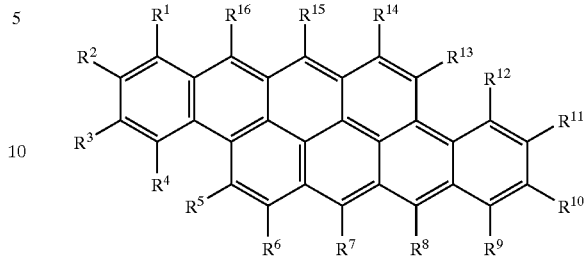

where $R^1$ through $R^{16}$ may be the same or may be different from each other, and represent hydrogen atoms or substituents;

Structural Formula (3)

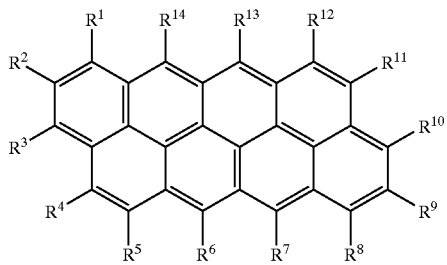

where $R^1$ through $R^{14}$ may be the same or may be different from each other, and represent hydrogen atoms or substituents.

31. An organic EL display according to claim 30, wherein the organic EL display is one of a passive matrix panel and an active matrix panel, and uses the organic EL element for emitting red light.

* * * * *

UNITED STATES PATENT AND TRADEMARK OFFICE
CERTIFICATE OF CORRECTION

PATENT NO. : 6,805,977 B2
DATED : October 19, 2004
INVENTOR(S) : Wataru Sotoyama et al.

It is certified that error appears in the above-identified patent and that said Letters Patent is hereby corrected as shown below:

<u>Title page,</u>
Item [56], References Cited, FOREIGN PATENT DOCUMENTS, change "0868 110" to -- 0866 110 --.
OTHER PUBLICATIONS, "Becker, Ralph S. et al." reference, change "Cheical" to -- Chemical --.

Signed and Sealed this

Seventeenth Day of May, 2005

JON W. DUDAS
*Director of the United States Patent and Trademark Office*